(12) United States Patent
Yang et al.

(10) Patent No.: US 12,702,383 B2
(45) Date of Patent: Aug. 11, 2026

(54) FILTERING AND APODIZATION COMBINATION FOR ULTRASOUND IMAGE GENERATION AND ASSOCIATED SYSTEMS, METHODS, AND DEVICES

(71) Applicant: PHILIPS IMAGE GUIDED THERAPY CORPORATION, San Diego, CA (US)

(72) Inventors: Yiqun Yang, Sacramento, CA (US); Andrew Hancock, Sacramento, CA (US); David Hope Simpson, Bothell, WA (US); Francois Guy Gerard Marie Vignon, Andover, MA (US); Jun Seob Shin, Winchester, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 45 days.

(21) Appl. No.: 18/286,467

(22) PCT Filed: Apr. 15, 2022

(86) PCT No.: PCT/EP2022/060186

§ 371 (c)(1),
(2) Date: Oct. 11, 2023

(87) PCT Pub. No.: WO2022/228922

PCT Pub. Date: Nov. 3, 2022

(65) Prior Publication Data

US 2024/0188933 A1 Jun. 13, 2024

Related U.S. Application Data

(60) Provisional application No. 63/179,678, filed on Apr. 26, 2021.

(51) Int. Cl.

*A61B 8/00* (2006.01)
*A61B 8/12* (2006.01)

(Continued)

(52) U.S. Cl.

CPC .............. *A61B 8/5207* (2013.01); *A61B 8/12* (2013.01); *A61B 8/4488* (2013.01); *A61B 8/463* (2013.01);

(Continued)

(58) Field of Classification Search

CPC .................................................. G01S 15/8927

See application file for complete search history.

(56) References Cited

U.S. PATENT DOCUMENTS

| | | | | |
|---|---|---|---|---|
| 5,544,659 A * | 8/1996 | Banjanin | G01S 7/52071 | 600/455 |
| 5,924,991 A * | 7/1999 | Hossack | G01S 15/8993 | 600/443 |

(Continued)

FOREIGN PATENT DOCUMENTS

WO 2019057592 A1 3/2019

OTHER PUBLICATIONS

International Search Report and Written Opinion of PCT/EP2022/060186, dated Jul. 26, 2022.

*Primary Examiner* — Pascal M Bui Pho
*Assistant Examiner* — Nyrobi Celestine

(57) ABSTRACT

An ultrasound imaging system may include an array of acoustic elements and a processor circuit. The array may be configured to transmit ultrasound energy and receive echoes. The processor circuit may be configured to generate first image data based on a first filtering and apodization of ultrasound signals associated with the received echoes and to generate second image data based on a second filtering and apodization of the ultrasound signals. The first image data is associated with a first resolution, and the second image data is associated with a second resolution. The processor circuit may be configured to generate an ultrasound image based on the first and second image data such that the ultrasound image includes a different, third resolu- (Continued)

tion, where each of the first, second, and third resolution includes a respective axial and a respective lateral resolution, and to output the ultrasound image to a display.

19 Claims, 19 Drawing Sheets

(51) Int. Cl.
*G01S 7/52* (2006.01)
*G01S 15/89* (2006.01)
(52) U.S. Cl.
CPC .............. *A61B 8/5269* (2013.01); *A61B 8/54* (2013.01); *G01S 15/8922* (2013.01); *G01S 15/8927* (2013.01); *G01S 7/52077* (2013.01)

(56) References Cited

U.S. PATENT DOCUMENTS 6,132,374 A * 10/2000 Hossack ............. G01S 7/52074 600/443
6,436,044 B1 * 8/2002 Wang .................. G01S 7/52047 600/443
6,436,049 B1 * 8/2002 Kamiyama ............ A61B 8/469 600/458
6,645,146 B1 * 11/2003 Adams ................ G01S 7/52038 600/443
7,846,101 B2 12/2010 Eberle
2003/0092992 A1 * 5/2003 Kawagishi ............. A61B 8/481 600/458
2005/0054929 A1 * 3/2005 Angelsen ............ G01S 15/8997 600/447
2007/0055160 A1 * 3/2007 Ng ...................... G01S 15/8961 600/447
2007/0213614 A1 * 9/2007 Suzuki ................... A61B 8/463 600/443
2009/0141957 A1 6/2009 Yen
2012/0289835 A1 * 11/2012 Hwang ............... G01S 7/52047 600/447
2013/0066210 A1 * 3/2013 Sumi .................... A61B 8/5207 600/447
2014/0303491 A1 * 10/2014 Shekhar .................. G06T 7/337 600/424
2016/0217574 A1 * 7/2016 Kang ................... A61B 8/5276
2017/0053396 A1 * 2/2017 Zhai ....................... A61B 8/467
2017/0108584 A1 * 4/2017 Oelze .................. G01S 7/52047
2017/0128050 A1 * 5/2017 Kang ..................... A61B 8/467
2017/0184713 A1 * 6/2017 Robert ................ G01S 15/8977
2018/0000452 A1 * 1/2018 Adams ................ G01S 7/52095
2019/0008485 A1 * 1/2019 Li ....................... G01S 15/8952
2020/0077984 A1 * 3/2020 Shin ..................... A61B 8/5269
2020/0081107 A1 * 3/2020 Shin .................... G01S 7/52047
2020/0129157 A1 * 4/2020 Demi .................. G01S 15/8927
2020/0245977 A1 * 8/2020 Hancock .............. A61B 8/4461
2021/0038320 A1 * 2/2021 Fox ...................... G01S 15/892

* cited by examiner 124
502k
502j
502i
502h
502g
502f
502e
502d
502c
502b
502a
502
502
510i
510b
510c
508
506
510a
504a
504b
504c
504

1640
1106
1406

1620
1106
1406

1600
1106
1406

FILTERING AND APODIZATION COMBINATION FOR ULTRASOUND IMAGE GENERATION AND ASSOCIATED SYSTEMS, METHODS, AND DEVICES

TECHNICAL FIELD

The subject matter described herein relates to a system for ultrasound imaging, such as intravascular ultrasound (IVUS) imaging, for example. In particular, the present disclosure describes combinations of filters and apodizations for generating of an ultrasound image with relatively high axial and/or lateral resolution.

BACKGROUND

Ultrasound images and, in particular, intravascular ultrasound images may be generated in a manner that provides relatively high contrast and/or maximizes contrast within the images. For instance, an intravascular ultrasound image may be generated such that dark regions of the image, which may correspond to blood flow within a vessel, are distinguishable from light regions of the image, which may correspond to the walls of the vessel and/or a stent positioned within the vessel. While the vessel walls and/or features of a stent may be distinguishable from regions of blood flow based on the contrast of an ultrasound image, a level of detail these features within the image is influenced by the resolution of the image. In this regard, relatively higher resolution images reveal more details of plaque morphology than relatively lower resolution images. As such, generating images with increased resolution may aid physicians and image interpreters in performing diagnostics, measurements, and treatment planning with greater precision and confidence.

SUMMARY

Disclosed are systems, methods, and devices for generating an ultrasound image with a relatively high axial resolution and/or lateral resolution. More specifically, generation of an ultrasound image based on a combination of filters and a combination of apodizations is disclosed herein. For example, an ultrasound imaging system may include a transducer array having a number of acoustic elements. The ultrasound imaging system may be configured to control the acoustic elements to transmit ultrasound energy and receive echoes associated with ultrasound energy. First image data and different, second image data may be generated based on ultrasound signals associated with the received echoes. In particular, the first image data may be generated based on a first combination of filtering and apodization of the ultrasound signals, while the second image data may be generated based on a second combination of filtering and apodization of the ultrasound signals. The first image data may be associated with a first resolution (e.g., a first axial resolution and a first lateral resolution). Moreover, the second combination of filtering and apodization of the ultrasound signals may be configured to generate second image data associated with a second resolution (e.g., a second axial resolution and a second lateral resolution). The second resolution may be different than the first resolution. More specifically, the second axial resolution may be different than the first axial resolution and/or the second lateral resolution may be different from the first lateral resolution. For instance, the second combination of filtering and apodization may correspond to a combination of whitened filtering and/or whitened apodization of the ultrasound signals. The whitened filtering of the ultrasound signals may improve the axial resolution of the second image data, the whitened apodization of the ultrasound signals may improve the lateral resolution of the second image data, and the combination of the whitened filtering and the whitened apodization may produce second image data and/or an ultrasound image with improved axial resolution and improved lateral resolution. Moreover, generating an image based on the first image data and the second image data may minimize artifacts that may be associated with the second combination of filtering and apodization, such as side lobes and/or Gibbs ringing, within a resulting ultrasound image. In this way, the ultrasound image may include a third resolution (e.g., a third axial resolution and a third lateral resolution) different than at least one of the first resolution or the second resolution. The ultrasound image may be generated based on a minimum intensity projection (MIP) with respect to the first image data and the second image data, for example.

In an exemplary aspect, an ultrasound imaging system includes an array of acoustic elements and a processor in communication with the array of acoustic elements. The array of acoustic elements may be configured to transmit ultrasound energy and receive echoes associated with the ultrasound energy. The processor circuit may configured to: generate first image data based on performing a first filtering and a first apodization of ultrasound signals associated with the received echoes, where the first image data is associated with a first resolution; generate different, second image data based on performing a second filtering and a second apodization of the ultrasound signals, where the second image data is associated with a second resolution; generate an ultrasound image based on the first image data and the second image data such that the ultrasound image includes a third resolution different than at least one of the first resolution or the second resolution, where each of the first resolution, the second resolution, and the third resolution includes a respective axial resolution and a respective lateral resolution; and output the generated ultrasound image to a display in communication with the processor circuit.

In some aspects, the first filtering of the ultrasound signals includes a first filter configured to emphasize a center frequency of the ultrasound signals with respect to an off-center frequency of the ultrasound signals. In some aspects, the second filtering of the ultrasound signals includes a second filter configured to emphasize the off-center frequency of the ultrasound signals with respect to the center frequency of the ultrasound signals. In some aspects, the processor circuit is configured to generate the ultrasound image further based on a minimum intensity projection (MIP) operation. In some aspects, the second filtering includes a depth-dependent filtering. In some aspects, at least one of a grating lobe or a Gibbs ringing artifact is reduced within the ultrasound image in comparison with the first image data or the second image data.

In some aspects, the processor circuit is further configured to: perform the first apodization with respect to a first aperture; and perform the second apodization with respect to a different, second aperture. In some aspects, the processor circuit is further configured to: generate third image data based on performing a third filtering and a third apodization of ultrasound signals, where the third image data is different than the first image data and the second image data, and where the processor circuit is configured to generate the ultrasound image further based on the third image data. In some aspects, the processor circuit is further configured to: adjust at least one of a gain of the first image data or a gain of the second image data such that a mean level intensity of the first image data and a mean level intensity of the second image data are equal. In some aspects, the processor circuit is configured to generate the first image data using a first signal pathway and generate the second image data using a second signal pathway. In some aspects, the processor circuit is configured to generate the ultrasound image further based on performing envelope detection. In some aspects, the processor circuit is configured to generate the ultrasound image further based on performing scan conversion. In some aspects, the processor circuit includes a graphics processing unit (GPU).

In some aspects, the first apodization includes a first apodization function configured to: weight ultrasound signals corresponding to a first subset of the array of acoustic elements with a first weight; and weight ultrasound signals corresponding to a different, second subset of the array of acoustic elements with a second weight less than the first weight, where the first subset corresponds to one or more acoustic elements within a distance to a center of an aperture and the second subset corresponds to one or more acoustic elements outside the distance. In some aspects, the second apodization includes a second apodization function configured to: weight the ultrasound signals corresponding to the first subset with a third weight; and weight the ultrasound signals corresponding to the second subset of the array of acoustic elements with a fourth weight greater than the third weight. In some aspects, the axial resolution of the third resolution exceeds the axial resolution of at least one of the first resolution or the second resolution and the lateral resolution of the third resolution exceeds the lateral resolution of at least one of the first resolution or the second resolution.

In an exemplary aspect, a method includes: controlling, by a processor circuit, an array of acoustic elements in communication with the processor circuit to transmit ultrasound energy and receive echoes associated with the ultrasound energy; generating, by the processor circuit, first image data based on performing a first filtering and a first apodization of ultrasound signals associated with the received echoes, where the first image data is associated with a first resolution; generating, by the processor circuit, different, second image data based on performing a second filtering and a second apodization of the ultrasound signals, where the second image data is associated with a second resolution; generating, by the processor circuit, an ultrasound image based on the first image data and the second image data such that the ultrasound image includes a third resolution different than at least one of the first resolution or the second resolution, where each of the first resolution, the second resolution, and the third resolution includes a respective axial resolution and a respective lateral resolution; and outputting, by the processor circuit, the generated ultrasound image to a display in communication with the processor circuit.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1:
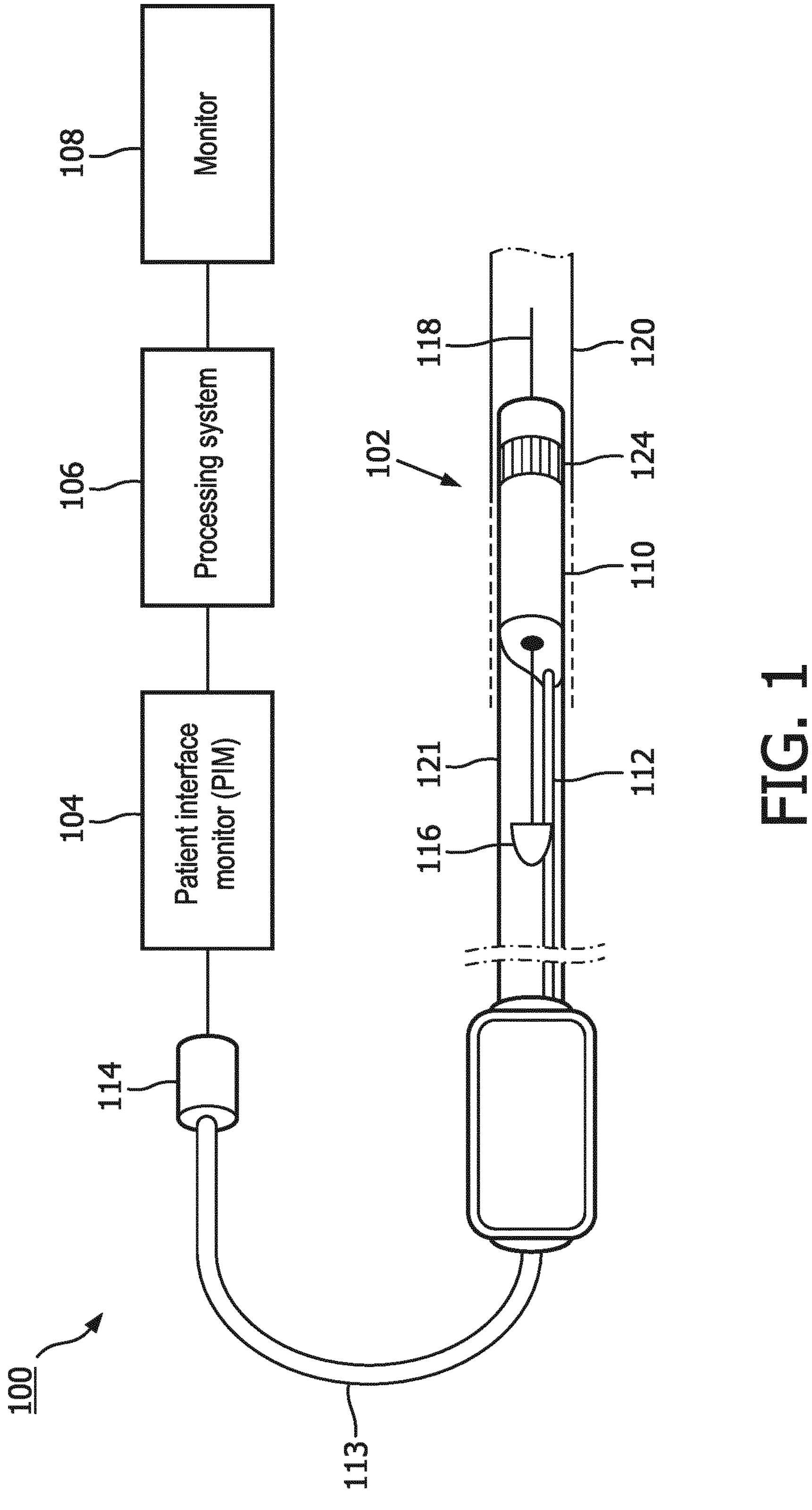
FIG. 1 is a diagrammatic schematic view of an ultrasound imaging system, according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a diagrammatic schematic view of an ultrasound imaging system 100, according to aspects of the present disclosure. The ultrasound imaging system 100 can be an intraluminal imaging system. In some instances, the system 100 can be an intravascular ultrasound (IVUS) imaging system. The system 100 may include an intraluminal imaging device 102 such as a catheter, guide wire, or guide catheter, a patient interface module (PIM) 104, a processing system 106 (e.g., console), and a monitor 108 (e.g., an electronic display). The intraluminal imaging device 102 can be an ultrasound imaging device. In some instances, the device 102 can be IVUS imaging device, such as a solid-state IVUS device.

At a high level, the IVUS device 102 emits ultrasonic energy, or ultrasound signals, from a transducer array 124 included in scanner assembly 110 mounted near a distal end of the catheter device. The ultrasonic energy is reflected by tissue structures in the medium, such as a vessel 120, or another body lumen surrounding the scanner assembly 110, and the ultrasound echo signals are received by the transducer array 124. In that regard, the device 102 can be sized, shaped, or otherwise configured to be positioned within the body lumen of a patient. The PIM 104 transfers the received echo signals to the processing system 106 (e.g., a console and/or computer) where the ultrasound image (possibly including flow information) is reconstructed and displayed on the monitor 108. The processing system 106 can include a processor and a memory. The processing system 106 can be operable to facilitate the features of the IVUS imaging system 100 described herein. For example, the processing system 106 can execute computer readable instructions stored on the non-transitory tangible computer readable medium.

The PIM 104 facilitates communication of signals between the processing system 106 and the scanner assembly 110 included in the IVUS device 102. This communication includes the steps of: (1) providing commands to integrated circuit controller chip(s) included in the scanner assembly 110 to select the particular transducer array element(s), or acoustic element(s), to be used for transmit and receive, (2) providing the transmit trigger signals to the integrated circuit controller chip(s) included in the scanner assembly 110 to activate the transmitter circuitry to generate an electrical pulse to excite the selected transducer array element(s), and/or (3) accepting amplified echo signals received from the selected transducer array element(s) via amplifiers included on the integrated circuit controller chip (s) of the scanner assembly 110. In some embodiments, the PIM 104 performs preliminary processing of the echo data prior to relaying the data to the processing system 106. In examples of such embodiments, the PIM 104 performs amplification, filtering, and/or aggregating of the data. In an embodiment, the PIM 104 also supplies high- and low-voltage DC power to support operation of the device 102 including circuitry within the scanner assembly 110.

The processing system 106 receives the echo data from the scanner assembly 110 by way of the PIM 104 and processes the data to reconstruct an image of the tissue structures in the medium surrounding the scanner assembly 110. The processing system 106 (e.g., a console) outputs image data such that an image of the vessel 120, such as a cross-sectional image of the vessel 120, is displayed on the monitor 108. Vessel 120 may represent fluid filled or surrounded structures, both natural and man-made. The vessel 120 may be within a body of a patient. The vessel 120 may be a blood vessel, as an artery or a vein of a patient's vascular system, including cardiac vasculature, peripheral vasculature, neural vasculature, renal vasculature, and/or or any other suitable lumen inside the body. For example, the device 102 may be used to examine any number of anatomical locations and tissue types, including without limitation, organs including the liver, heart, kidneys, gall bladder, pancreas, lungs; ducts; intestines; nervous system structures including the brain, dural sac, spinal cord and peripheral nerves; the urinary tract; as well as valves within the blood, chambers or other parts of the heart, and/or other systems of the body. In addition to natural structures, the device 102 may be used to examine man-made structures such as, but without limitation, heart valves, stents, shunts, filters and other devices.

In some embodiments, the IVUS device includes some features similar to traditional solid-state IVUS catheters, such as the EagleEye® catheter available from Koninklijke Philips N.V. and those disclosed in U.S. Pat. No. 7,846,101 hereby incorporated by reference in its entirety. For example, the IVUS device 102 includes the scanner assembly 110 near a distal end of the device 102 and a transmission line bundle 112 extending along the longitudinal body of the device 102. The transmission line bundle or cable 112 can include a plurality of conductors, including one, two, three, four, five, six, seven, or more conductors. Further, in some embodiments, the IVUS device 102 includes a plurality of transmission line bundles each comprising a plurality of conductors of varying size (e.g., gauge), insulation, and/or other structural and electrical characteristics. It is understood that any suitable gauge wire can be used for the conductors. In an embodiment, the cable 112 can include a four-conductor transmission line arrangement with, e.g., 41 AWG gauge wires. In an embodiment, the cable 112 can include a seven-conductor transmission line arrangement utilizing, e.g., 44 AWG gauge wires. In some embodiments, 43 AWG gauge wires can be used.

The transmission line bundle 112 passes through or connects to a cable 113 that terminates in a PIM connector 114 at a proximal end of the device 102. The PIM connector 114 electrically couples the transmission line bundle 112 to the PIM 104 and physically couples the IVUS device 102 to the PIM 104. In an embodiment, the IVUS device 102 further includes a guide wire exit port 116. Accordingly, in some instances the IVUS device is a rapid-exchange catheter. The guide wire exit port 116 allows a guide wire 118 to be inserted towards the distal end in order to direct the device 102 through the vessel 120.

In an embodiment, the processing system 106 generates flow data by processing the echo signals from the IVUS device 102 into Doppler power or velocity information. The processing system 106 may also generate B-mode data by applying envelope detection and logarithmic compression on the conditioned echo signals. The processing system 106 can further generate images in various views, such as 2D and/or 3D views, based on the flow data or the B-mode data. The processing system 106 can also perform various analyses and/or assessments. For example, the processing system 106 can apply virtual histology (VH) techniques, for example, to analyze or assess plaques within a vessel (e.g., the vessel 120). The images can be generated to display a reconstructed color-coded tissue map of plaque composition superimposed on a cross-sectional view of the vessel.

In an embodiment, the processing system 106 can apply a blood flow detection algorithm to determine the movement of blood flow, for example, by acquiring image data of a target region (e.g., the vessel 120) repeatedly and determining the movement of the blood flow from the image data. The blood flow detection algorithm operates based on the principle that signals measured from vascular tissue are relatively static from acquisition to acquisition, whereas signals measured from blood flow vary at a characteristic rate corresponding to the flow rate. As such, the blood flow detection algorithm may determine movements of blood flow based on variations in signals measured from the target region between repeated acquisitions. To acquire the image data repeatedly, the processing system 106 may control to the device 102 to transmit repeated pulses on the same aperture.

While the present disclosure describes embodiments related to intravascular ultrasound (IVUS) imaging using an intravascular catheter or guidewire, it is understood that one or more aspects of the present disclosure can be implemented in any suitable ultrasound imaging system, including a synthetic aperture ultrasound imaging system, a phased array ultrasound imaging system, or any other array-based ultrasound imaging system. For example, aspects of the present disclosure can be implemented in intraluminal ultrasound imaging systems using an intracardiac (ICE) echocardiography catheter and/or a transesophageal echocardiography (TEE) probe, and/or external ultrasound imaging system using an ultrasound probe configured for imaging while positioned adjacent to and/or in contact with the patient's skin. The ultrasound imaging device can be a transthoracic echocardiography (TTE) imaging device in some embodiments.

An ultrasound transducer array 124 of the ultrasound imaging device includes an array of acoustic elements configured to emit ultrasound energy and receive echoes corresponding to the emitted ultrasound energy. In some instances, the array 124 may include any number of ultrasound transducer elements. For example, the array can include between 2 acoustic elements and 10000 acoustic elements, including values such as 2 acoustic elements, 4 acoustic elements, acoustic elements, 64 acoustic elements, 128 acoustic elements, 500 acoustic elements, 812 acoustic elements, 3000 acoustic elements, 9000 acoustic elements, and/or other values both larger and smaller. In some instances, the transducer elements of the array 124 may be arranged in any suitable configuration, such as a linear array, a planar array, a curved array, a curvilinear array, a circumferential array, an annular array, a phased array, a matrix array, a one-dimensional (1D) array, a 1.x dimensional array (e.g., a 1.5D array), or a two-dimensional (2D) array. The array of transducer elements (e.g., one or more rows, one or more columns, and/or one or more orientations) can be uniformly or independently controlled and activated. The array 124 can be configured to obtain one-dimensional, two-dimensional, and/or three-dimensional images of patient anatomy.

The ultrasound transducer elements may include piezoelectric/piezoresistive elements, piezoelectric micromachined ultrasound transducer (PMUT) elements, capacitive micromachined ultrasound transducer (CMUT) elements, and/or any other suitable type of ultrasound transducer elements. The ultrasound transducer elements of the array are in communication with (e.g., electrically coupled to) electronic circuitry. For example, the electronic circuitry can include one or more transducer control logic dies. The electronic circuitry can include one or more integrated circuits (IC), such as application specific integrated circuits (ASICs). In some embodiments, one or more of the ICs can include a microbeamformer (μBF). In other embodiments, one or more of the ICs includes a multiplexer circuit (MUX).

Figure 2:
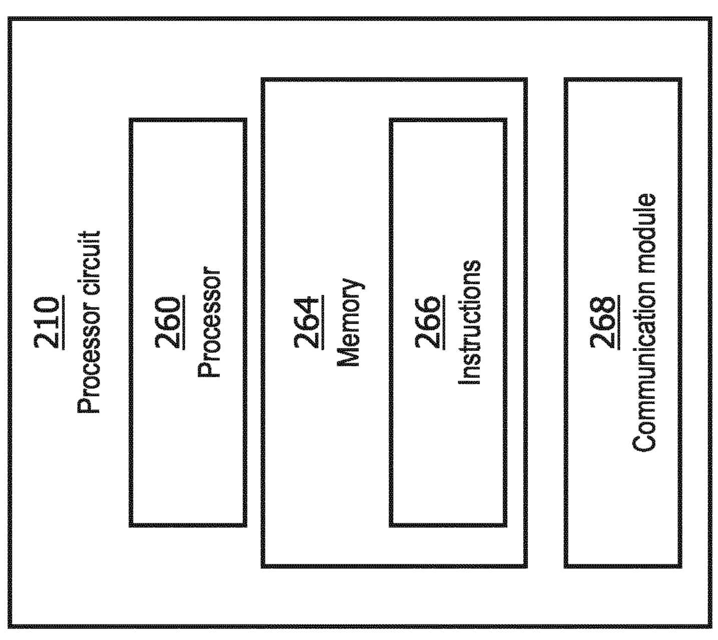
FIG. 2 is a schematic diagram of a processor circuit, according to aspects of the present disclosure.

FIG. 2 is a schematic diagram of a processor circuit 210, according to embodiments of the present disclosure. The processor circuit 210 may be implemented in the processing system 106 and/or the imaging device 102 of FIG. 1. As shown, the processor circuit 210 may include a processor 260, a memory 264, and a communication module 268. These elements may be in direct or indirect communication with each other, for example via one or more buses.

The processor 260 may include a central processing unit (CPU), a digital signal processor (DSP), an ASIC, a controller, an FPGA, another hardware device, a firmware device, or any combination thereof configured to perform the operations described herein. The processor 260 may also be implemented as a combination of computing devices, e.g., a combination of a DSP and a microprocessor, a plurality of microprocessors, one or more microprocessors in conjunction with a DSP core, or any other such configuration.

The memory 264 may include a cache memory (e.g., a cache memory of the processor 260), random access memory (RAM), magnetoresistive RAM (MRAM), read-only memory (ROM), programmable read-only memory (PROM), erasable programmable read only memory (EPROM), electrically erasable programmable read only memory (EEPROM), flash memory, solid state memory device, hard disk drives, other forms of volatile and non-volatile memory, or a combination of different types of memory. In an embodiment, the memory 264 includes a non-transitory computer-readable medium. The memory 264 may store instructions 266. The instructions 266 may include instructions that, when executed by the processor 260, cause the processor 260 to perform the operations described herein with reference to the processing system 106 and/or the imaging device 102 (FIG. 1). Instructions 266 may also be referred to as code. The terms "instructions" and "code" should be interpreted broadly to include any type of computer-readable statement(s). For example, the terms "instructions" and "code" may refer to one or more programs, routines, sub-routines, functions, procedures, etc. "Instructions" and "code" may include a single computer-readable statement or many computer-readable statements.

The communication module 268 can include any electronic circuitry and/or logic circuitry to facilitate direct or indirect communication of data between the processor circuit 210, the imaging device 102, and/or the monitor 108. In that regard, the communication module 268 can be an input/output (I/O) device. In some instances, the communication module 268 facilitates direct or indirect communication between various elements of the processor circuit 210 and/or the processing system 106 (FIG. 1).

Figure 3:
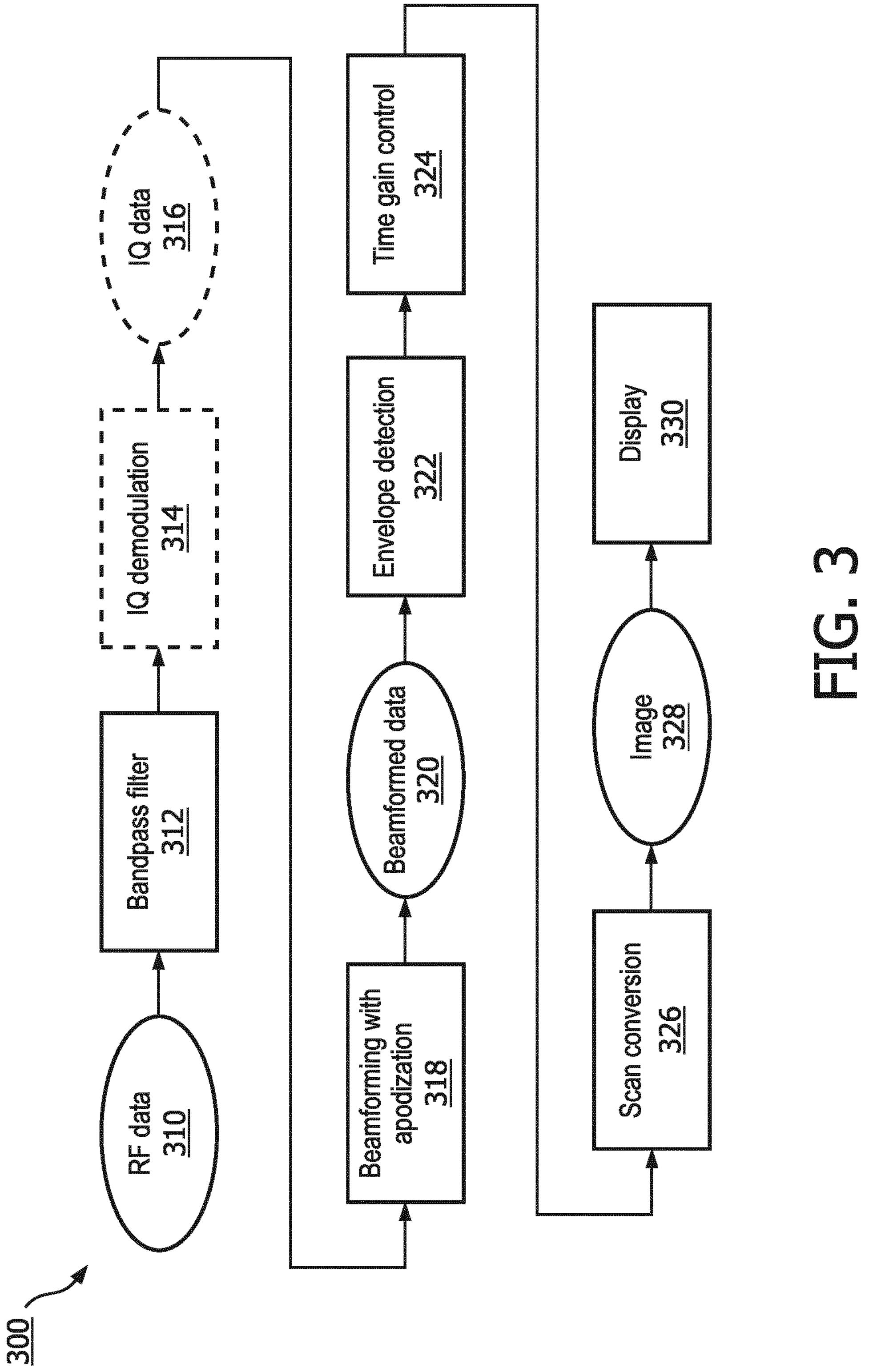
FIG. 3 is a block diagram of a signal pathway for generating an ultrasound image, according to aspects of the present disclosure.

FIG. 3 is a block diagram of a signal pathway 300 for generating an ultrasound image using a first filter and a first apodization, according to embodiments of the present disclosure. The signal pathway 300 may be associated with a method, or process, for image generation. It will be understood that the elements of the signal pathway 300 may comprise computer program code or instructions executable by a processor circuit, such as the processor circuit 210 shown in FIG. 2. For example, in some embodiments, the elements of the signal pathway 300 comprise different processing (e.g., software) modules. In some embodiments, the elements of the signal pathway 300 comprise different hardware components.

In some embodiments, the components and/or operations of the signal pathway 300 are implemented by the intraluminal imaging device 102, the PIM 104, and/or the processing system 106 shown in FIG. 1. In particular, components of the signal pathway 300 may be implemented by a beamformer and/or a processor circuit, such as processor circuit 210, included in the intraluminal imaging device 102, the PIM 104, and/or the processing system 106. In some embodiments, for example, the components of the signal pathway 300 are distributed between the intraluminal imaging device 102, the PIM 104, and/or the processing system 106. Moreover, the components of the signal pathway 300 can be implemented via a combination of hardware and software components, and may be executed by the processor circuit 210 described above with respect to FIG. 2. For instance, in some embodiments, one or more components and/or operations of the signal pathway 300 can be executed by a graphics processing unit (GPU) or a field-programmable gate array (FPGA).

In some embodiments, ultrasound data may be received (e.g., input to) to the signal pathway 300. For instance, the signal pathway 300 may receive ultrasound data and/or ultrasound signals based on received echoes associated with ultrasound energy transmitted by an array of acoustic elements (e.g., transducer array 124). The ultrasound data may include analog or digital data. For instance, in some cases, the signal pathway 300 may receive raw analog electrical signals from the array of acoustic elements. In such cases, one or more of the operations of the signal pathway 300 may be performed on the analog signals. Additionally or alternatively, the signal pathway 300 may include or be in communication with an analog-to-digital converter (ADC), which may sample the analog signals to provide digital ultrasound data. Further, as illustrated, the ultrasound data may be radio-frequency (RF) data 310. In some embodiments the ultrasound data may be complex-valued data, such as quadrature (IQ) data.

As illustrated, the signal pathway 300 may include a filter, such as bandpass filter 312, configured to filter the RF data 310. In particular, the signal pathway 300 may include a filter configured to pass a first set of frequencies of the RF data 310 such that the first set of frequencies is emphasized with respect to a different, second set of frequencies of the RF data 310. For instance, the filter may de-emphasize the second set of frequencies with respect to the first set of frequencies. In some embodiments, the filter may de-emphasize frequencies associated with noise and may emphasize frequencies associated with a signal, such as frequencies corresponding to an imaged feature within the RF data 310. As a result, the filter may increase the signal-to-noise ratio (SNR) associated with the ultrasound image output by the signal pathway 300. An example of emphasized frequencies (e.g., the first set of frequencies) and de-emphasized frequencies (e.g., the second set of frequencies) is described below with respect to an exemplary frequency response in FIG. 4.

Figure 4:
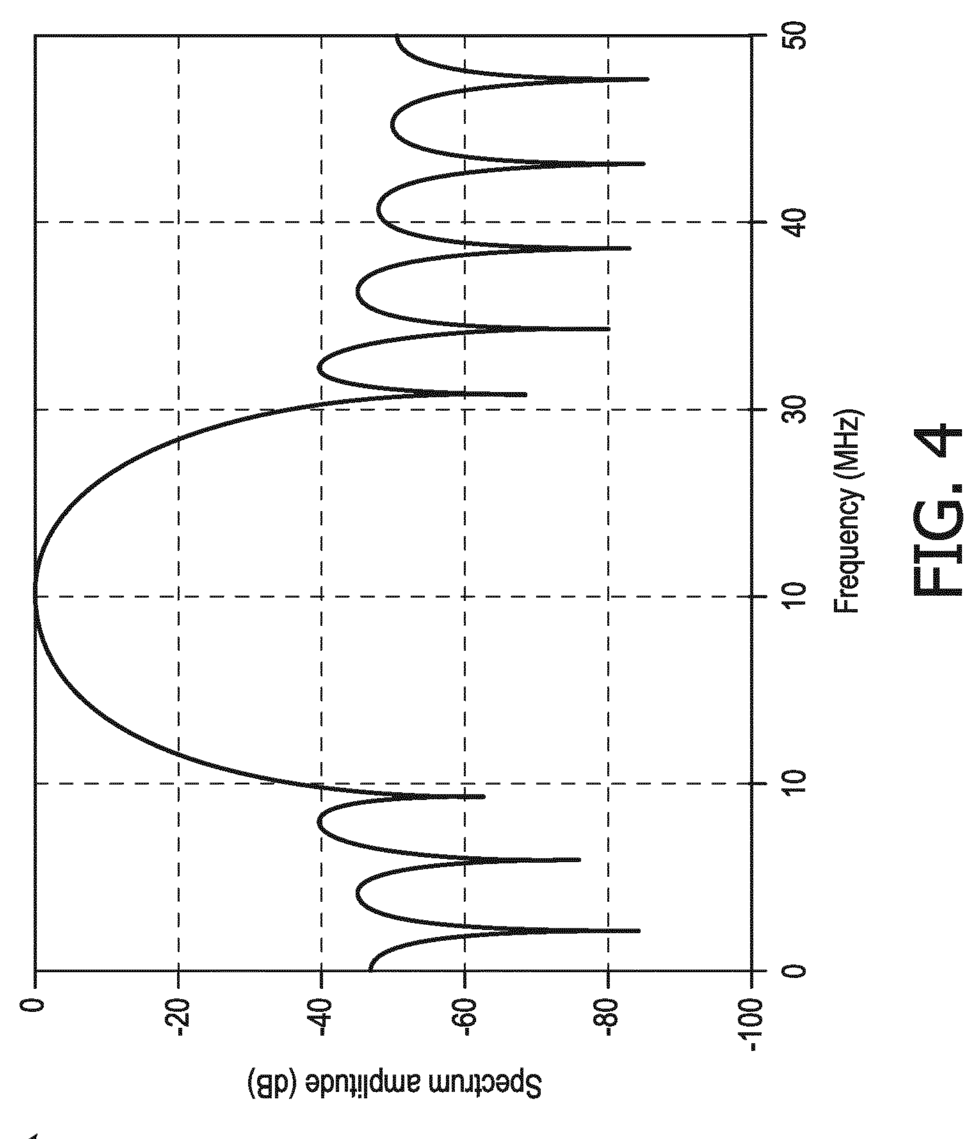
FIG. 4 is a plot of a frequency response of a filter, according to aspects of the present disclosure.
Figure 4:
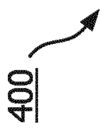

With reference now to FIG. 4, a plot 400 of a frequency response of a regular filter is illustrated. As described herein, the term "regular filter" may refer to a filter configured to pass a center frequency, such as a center frequency of ultrasound data, such that the center frequency is emphasized with respect to an off-center frequency, such as an off-center frequency of the ultrasound data. The plot 400 thus illustrates a frequency response of a regular bandpass filter. In an exemplary embodiment, bandpass filter 312 may be referenced as a regular filter, and as such, bandpass filter 312 may exhibit a frequency response similar to the plot 400. As shown, the frequency response is plotted against spectrum amplitude in decibels (dB) on a y-axis of the plot 400 and frequency in megahertz (MHz) on an x-axis of the plot 400. As further shown, the filter is configured to pass frequencies at approximately 20 MHz such that frequencies at approximately 20 MHz are emphasized with respect to frequencies less than and greater than approximately 20 MHz, such as 15 MHz and 25 MHz. Moreover, in some embodiments, the filter may be configured to emphasize a center frequency associated with ultrasound data input to the filter, such as RF data 310, with respect to an off-center frequency of the ultrasound data (e.g., and/or to de-emphasize the off-center frequency). That is, for example, the center frequency emphasized by the filter may be the center frequency of the transducer array 124.

Turning back now to FIG. 3, characteristics (e.g., gain, passed and/or attenuated frequency ranges, emphasized and/or de-emphasized frequency ranges, and/or the like) of the bandpass filter 312 may be tuned based on the transducer array 124 and/or the ultrasound data. In some embodiments, for example, the bandpass filter 312 may be configured to pass and emphasize a center frequency of the transducer array 124 and to de-emphasize an off-center frequency of the array 124. For example, in the plot 400 shown in FIG. 4, which may be an exemplary frequency response of the bandpass filter 312, the center frequency of the transducer array 124 may be 20 MHz and may be emphasized by the bandpass filter 312 with respect to off-center frequencies. The center frequency of 20 MHz is exemplary and not limiting. In that regard, the bandpass filter 312 may be configured to pass any suitable sets of frequencies such that they are emphasized with respect to other frequencies. Moreover, while the signal pathway 300 is illustrated as including the bandpass filter 312, it may be appreciated that any suitable filter, such as a low pass filter, a high pass filter, and/or the like may be additionally or alternatively included in the signal pathway 300. Further, the bandpass filter 312 may be implemented as an analog or a digital filter. In that regard, the bandpass filter 312 may be implemented as any suitable filter, such as a finite impulse response (FIR) filter, an infinite impulse response (IIR) filter, and/or the like. The bandpass filter 312 further may be implemented by a processor circuit (e.g., processor circuit 210), such as a GPU or an FPGA.

The signal pathway 300 may optionally include (e.g., as indicated by dashed lines) an IQ demodulation module 314. The IQ demodulation module 314 may be configured to perform a baseband conversion and/or demodulation on data within the signal pathway 300 (e.g., on the filtered RF data 310 output by the bandpass filter 312). In some embodiments, the IQ demodulation module 314 may include a rectifier configured to convert the real-valued RF samples in the ultrasound image signals (e.g., the RF data 310) to baseband (BB) signal signals and/or data including complex in-phase, quadrature-phase (IQ) pairs. The rectifier may perform down-conversion, low-pass filtering, and/or decimation. The down-conversion converts the RF data 310 to BB, for example, by down-mixing the RF data 310 with two sinusoidal signals with a 90 degrees phase difference. In some embodiments, a processor circuit, such as processor circuit 210 of FIG. 2, may implement the IQ demodulation module 314. In some embodiments, for example, a GPU may perform demodulation on RF data 310.

As further illustrated, the IQ demodulation module 314 may output IQ data 316. In this regard, the signal pathway 300 may be configured to operate within the real and/or complex domain (e.g., using the RF data 310 and/or the IQ data 316, respectively).

The signal pathway 300 may further involve apodization of the ultrasound signals associated with echoes received from the transducer array 124 (e.g., apodization of RF data and/or IQ data). As illustrated, for example, the signal pathway 300 may include a beamforming with apodization operation 318. At a high level, the beamforming with apodization operation 318 involves apodizing and beamforming (e.g., delay and summing) ultrasound data associated with a particular aperture of the transducer array 124. More specifically, the beamforming with apodization operation 318 involves applying an apodization function to the ultrasound data associated with the aperture. The beamforming with apodization operation 318 may further refer to beamforming and apodization with respect to an aperture that includes a first quantity of elements, such as a 14-element transmit aperture and a 14-element receive aperture. Apertures and apodization of image data is described in greater detail below with reference to FIGS. 5, 6, and 7A-7C.

Further, in an exemplary embodiment, the beamforming with apodization operation 318 may be referenced as a beamforming with regular apodization operation. As described herein, the term "regular apodization" may refer to application of an apodization function configured to emphasize ultrasound data corresponding to center elements (e.g., transducer elements) of the aperture and to de-emphasize ultrasound data corresponding to off-center and/or edge elements of the aperture.

Figure 5:
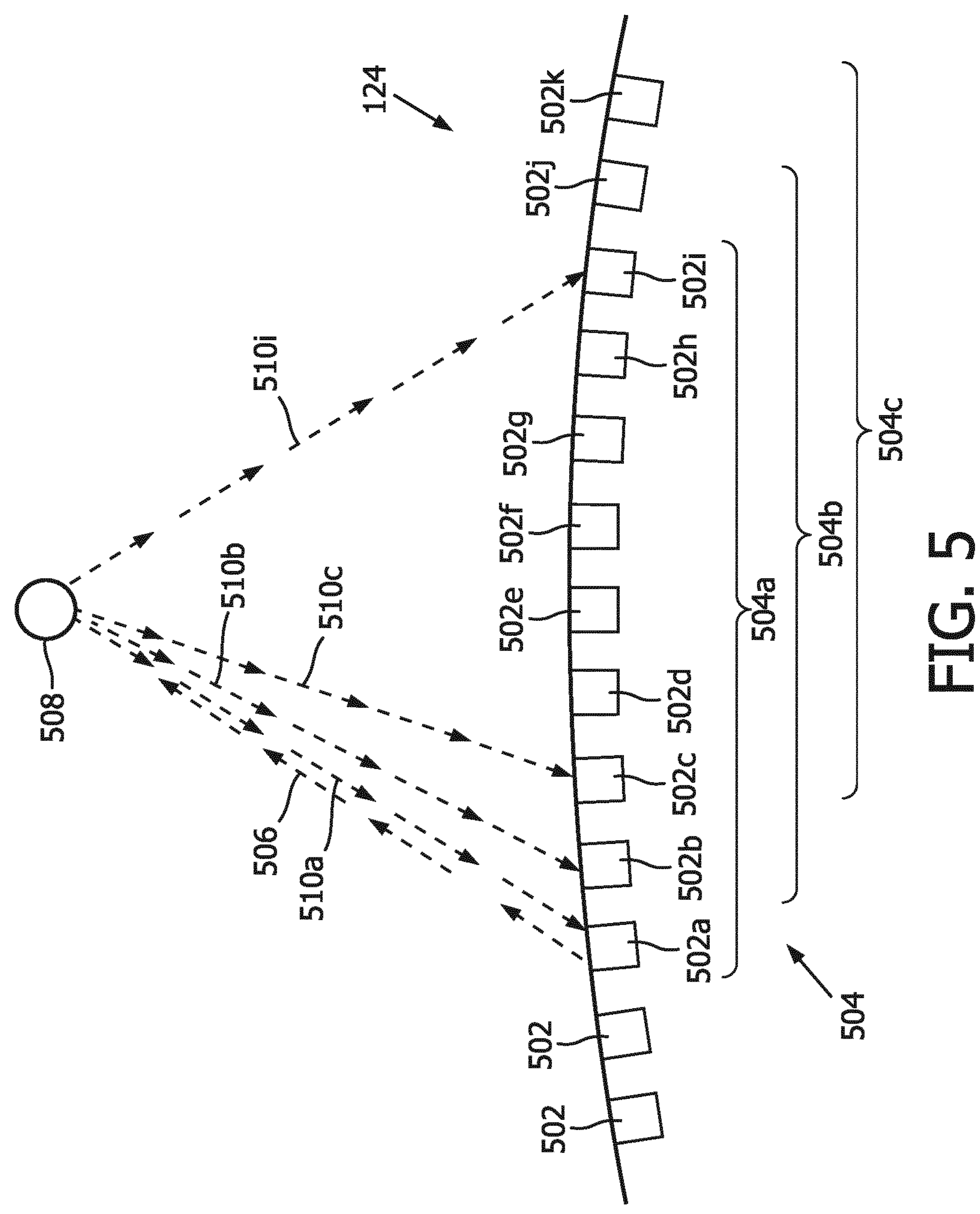
FIG. 5 is an aperture diagram of a transducer array, according to aspects of the present disclosure.
Figure 6:
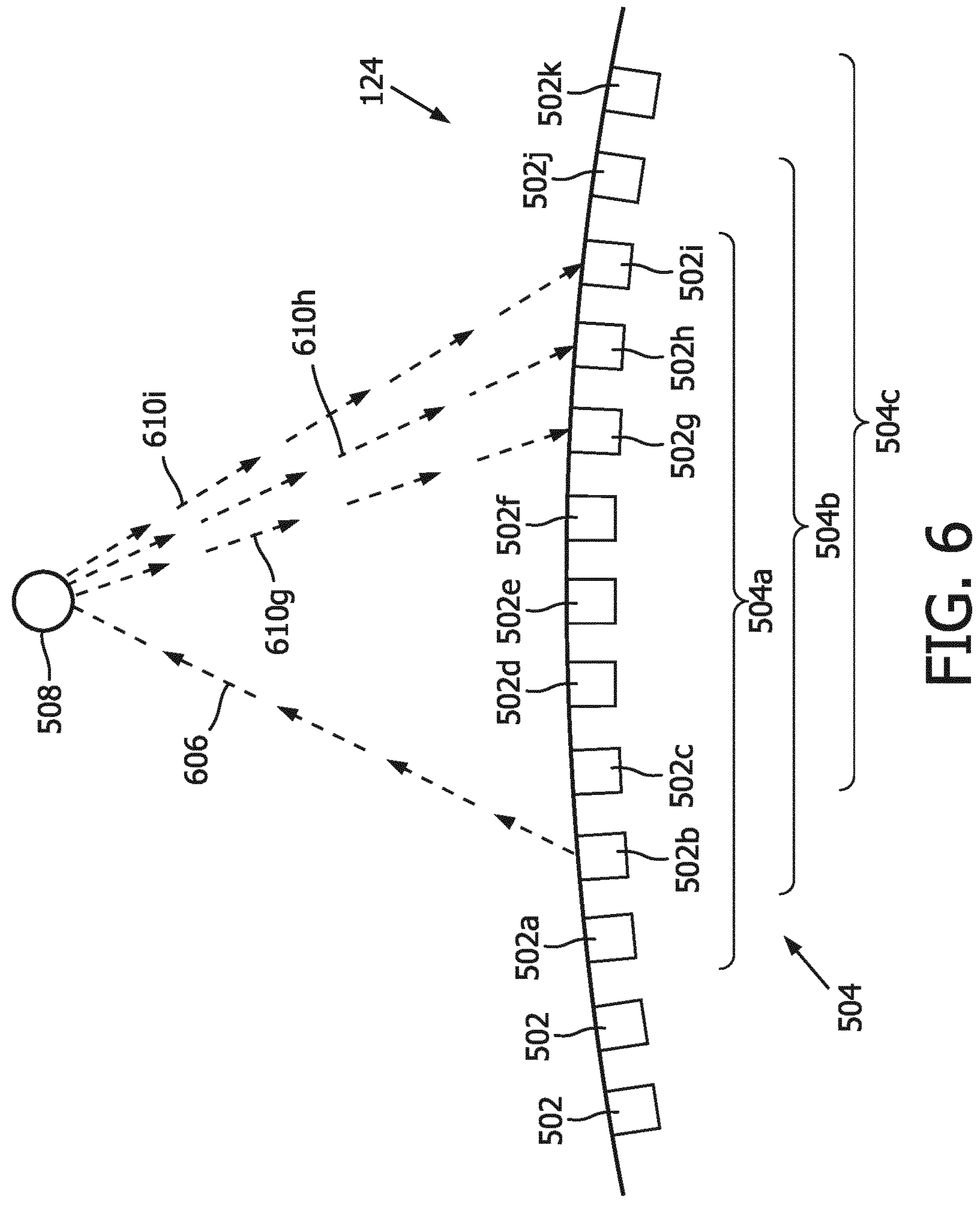
FIG. 6 is an aperture diagram of a transducer array, according to aspects of the present disclosure.

FIGS. 5 and 6 illustrate the collection of ultrasound data using one or more apertures according to aspects of the present disclosure. In particular, FIGS. 5 and 6 are radial cross-sectional views of a portion of the transducer array 124, which includes a quantity of transducers 502, thirteen of which are illustrated. The transducers 502 are grouped into apertures 504, including apertures 504*a*, 504*b*, and 504*c*. In some embodiments, each transducer 502 may be part of one or more apertures 504. For example, transducer 502*c* is included in apertures 504*a*, 504*b*, and 504*c*. By way of non-limiting example, in the illustrated embodiment, each aperture 504 contains nine transducers 502. Other aperture widths are contemplated. For example, further embodiments have apertures 504 containing 8, 10, 12, 14, 16, 20, or 32 transducers 502. In an embodiment, an aperture 504 contains 128 transducers 502.

To collect ultrasound data, groupings of emitting (e.g., transmitting) and receiving transducers, which are referred to as A-lines, may be designated within an aperture 504. For example, with respect to exemplary aperture 504*a*, which includes transducer 502*a* at a first end and transducer 502*i* located at a second end, transducer 502*a* may be designated as a first emitting and receiving transducer. As an emitting transducer, the transducer 502*a* may be triggered to emit ultrasonic energy. A portion of the ultrasonic energy (e.g., the portion directed along the line indicated by arrows 506) is then reflected by a target structure 508 located in the environment surrounding the transducer array 124. A designated receiving transducer (in the current example, transducer 502*a*) or transducers then receive the reflected ultrasonic echo (indicated by arrows 510*a*). For the purposes of this disclosure, the act of receiving by a transducer may include experiencing an energy impulse such as an ultrasonic echo, converting the received impulse into a signal such as an electric potential, transmitting the converted signal, measuring the converted signal, and/or other suitable receiving steps. In some embodiments, a plurality of emitting transmitters is fired as a group. Firing transducers as a group may create a stronger ultrasonic transmission. Particularly in, but not limited to, embodiments using relatively small emitting transducers and/or embodiments imaging relatively long distances, a stronger emission improves the signal-to-noise ratio. Similarly, in some embodiments, a plurality of receiving transducers is set to receive as a group. The group of transducers may produce a stronger electrical potential with better imaging characteristics than individual transducers acting alone.

In the illustrated embodiment, a sequence of firings is produced for each emitting transducer using a series of receiving transducers. The receiving transducers are stepped through according to a walk pattern. An exemplary walk pattern, which may be designated a forward walk, advances designation of transducers in an arbitrary first direction (e.g., from transducer 502*a* to 502*b* to 502*c*). A backward walk advances transducers in a direction opposite the first direction (e.g., from transducer 502*c* to 502*b* to 502*a*). Other walk patterns utilize more than one direction, skip transducers, repeat transducers, group transducers and/or operate according to any other suitable pattern.

The walk pattern illustrated in FIG. 5 is a forward walk. For instance, continuing with the example of the emitting transducer 502*a*, the designated receiving transducer configured to receive the ultrasonic energy reflected back by the target structure 508 advances from transducer 502*a*, which receives the reflected ultrasonic echo indicated by arrows 510*a*, to 502*b*, which receives the reflected ultrasonic echo indicated by arrows 510*b*, to 502*c*, which receives the reflected ultrasonic echo indicated by arrows 510*c*. When the receive cycle is complete, the next emitting transducer is selected. For example, the emitting transducer may transition from being the transducer 502*a* to 502*b*. The transmit and receive sequence may then be repeated using the newly designated emitting transducer paired with the various, stepped through receivers.

Referring now to FIG. 6, in the illustrated embodiment, transducer 502*b* is designated the next emitting transducer, and the receiver walk pattern is shown as a backward walk pattern. In this embodiment, transducer 502*i* is an initially designated receiving transducer. As illustrated, emitting transducer 502*b* creates an ultrasound emission (indicated by arrows 606), which is reflected by the target structure 508 and received by transducer 502*i* (indicated by arrows 610*i*). Because of the backward walk pattern, in the next iteration, the emissions from transducer 502*b* are received by transducer 502*h* (indicated by arrows 610*h*) and subsequently transducer 502*g* (indicated by arrows 610*g*). The process continues until final emitting transducer has completed a receive cycle, and, in some embodiments, the A-line combinations of emitting transducers and receiving transducers within the aperture are exhausted.

It is understood that the description of ultrasound data collection in terms of stepping through receiving transducer for a designated emitting transducer is purely arbitrary. In some embodiments, a receiving transducer is designated and a sequence of emitting transducers are proceeded through before a new receiving transducer is designated. Furthermore, the emitter and receiver walk patterns disclosed with reference to FIGS. 5-6 are examples selected for clarity of illustration. Other walk patterns are contemplated and provided for.

As can be seen, for each of the exemplary nine-transducer apertures 504, 81 transducer combinations (or A-lines) exist. In some embodiments, the number of A line firings is reduced by assuming that A-line data exhibits a reciprocal nature. In other words, a signal emitted by transducer 502*a* and received by transducer 502*i* may be a suitable substitute for a signal emitted by transducer 502*i* and received by transducer 502*a*. Thus, in some embodiments, only one A line for each reciprocal A line pair is generated.

Figures 7A, 7B, 7C:
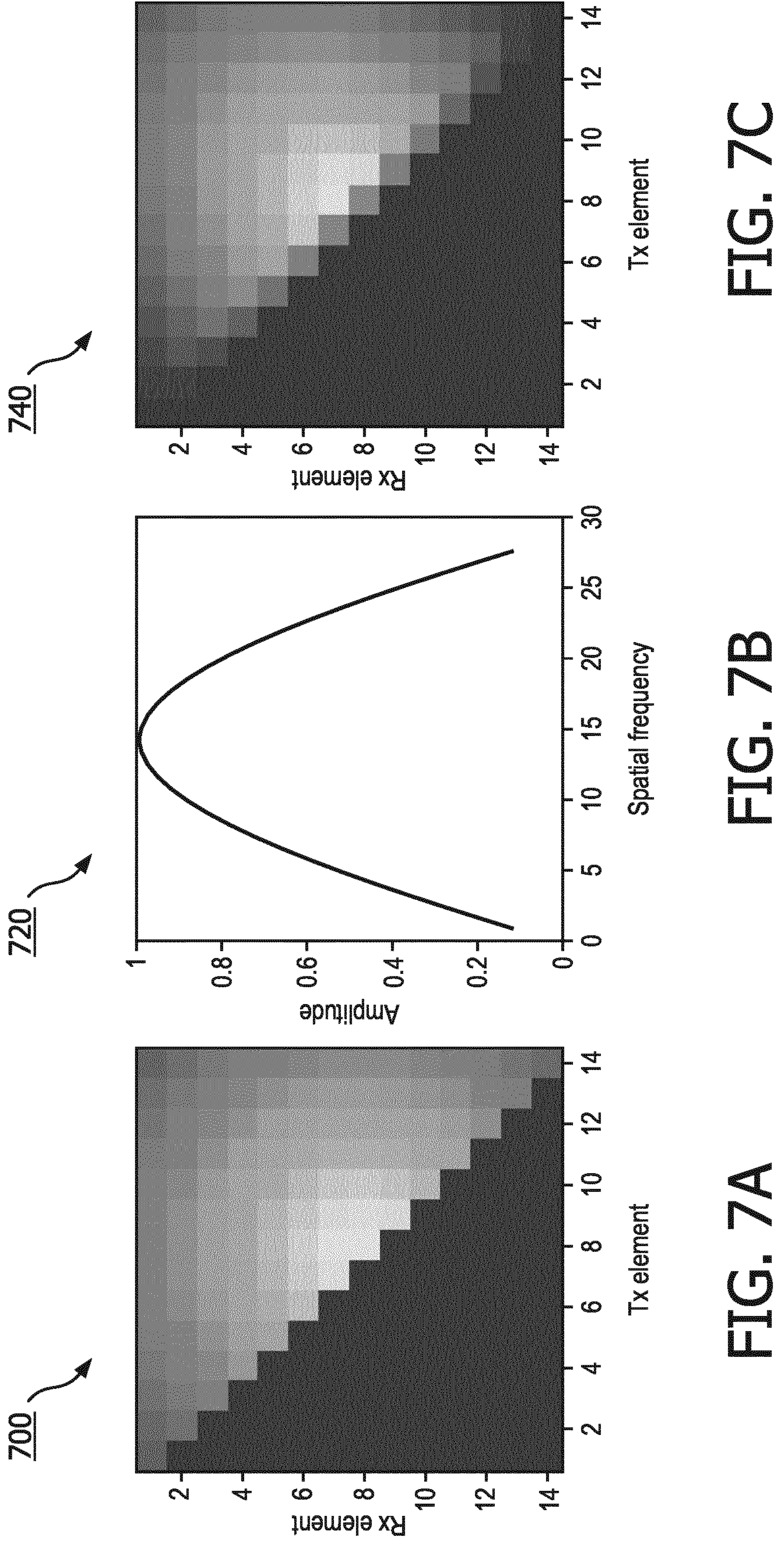
FIG. 7A is an element directivity map, according to aspects of the present disclosure.
FIG. 7B is a plot of an apodization function, according to aspects of the present disclosure, according to aspects of the present disclosure.
FIG. 7C is an element directivity map, according to aspects of the present disclosure.

FIG. 7A is an element directivity map 700 (e.g., an aperture diagram) according to aspects of the present disclosure. The element directivity map 700 illustrates the relationship between transducer pairs (A-lines), where the x-axis indicates the transducer used to transmit ultrasound energy (e.g., the transmit (Tx) element) and the y-axis indicates the transducer element used to receive echoes associated with the transmitted ultrasound energy (e.g., the receive (Rx) element). While the apertures 504 illustrated in FIGS. 5-6 are illustrated and described as using 9 elements (e.g., transducers 502) to both transmit and receive data, the element directivity map 700 is illustrated with respect to an aperture that uses 14 elements to both transmit ultrasound energy and receive echoes associated with the transmitted ultrasound energy (e.g., a 14-element transmit aperture and a 14-element receive aperture, respectively). The elements within the illustrated aperture are numbered 1 through 14, where transducer 1 may be positioned at a first end of the aperture and transducer 14 may be positioned at a second end of the aperture.

The element directivity map 700 indicates an intensity level of received echoes associated with transmitted ultrasound energy (e.g., an intensity level of the A-lines) via grayscale color-coding. In particular, the whiter (e.g., brighter and/or lighter) regions of the element directivity map 700 indicate a relatively higher intensity level, while the darker (e.g., increasingly black) regions of the element directivity map indicate a relatively lower intensity level. As further illustrated, the element directivity map 700 includes intensity levels for a subset (e.g., approximately half) of the combinations of transmit and receive elements. In particular, the element directivity map 700 is illustrated with only one A-line for each reciprocal A-line pair (e.g., a reciprocal transducer, receiver element pair). To that end, the illustrated intensity for a particular transmitter element and a receiver element pair may be a suitable substitute for (e.g., estimate of) the intensity of the reciprocal transmitter and receiver element pair illustrated without an intensity level (e.g., indicated as black) within the element directivity map 700, as described above. As an illustrative example, the intensity of the A-line where transducer element 14 is the transmit element and transducer element 1 is the receive element may be representative of the A-line where the transducer element 1 is the transmit element and the transducer element 14 is the receive element. In some embodiments, A-line data (e.g., intensities) may additionally or alternatively be obtained and/or displayed in an element directivity map for each pair of transmit and receive element pairs. As further illustrated, the element directivity map 700 shows that an intensity of ultrasound data associated with groupings of transmit and receive transducer elements within the center of an aperture is greater than an intensity of ultrasound data associated with groupings of transmit and receive transducer elements that are off-center, such as edge elements.

FIG. 7B is a plot 720 of an apodization function according to aspects of the present disclosure. As illustrated, an x-axis of the plot 720 is spatial frequency in arbitrary units, and a y-axis of the plot 720 is amplitude in arbitrary units. The plot 720 illustrates an apodization function that may be applied to ultrasound data, such as RF data 310 and/or IQ data 316, for the beamforming with apodization operation 318 of FIG. 3. In particular, the plot 720 illustrates an apodization function configured to emphasize ultrasound data corresponding to center elements (e.g., transducer elements) of the aperture and to de-emphasize ultrasound data corresponding to off-center elements of the aperture. In this regard, the illustrated apodization function is configured to emphasize a spatial frequency corresponding to the center elements of the aperture and to de-emphasize the spatial frequencies corresponding to the off-center and/or edge elements of the aperture, as shown by the plot 720. That is, for example, the apodization function may apply a first weight (e.g., gain) to ultrasound data corresponding to the center elements and may apply a different, second weight to the ultrasound data corresponding to the off-center and/or edge elements, where the second weight is less than the first weight.

A non-limiting example of an apodization function configured to emphasize ultrasound data corresponding to center elements of the aperture and to de-emphasize ultrasound data corresponding to off-center elements of the aperture is a raising cosine function, which is illustrated in the plot 720 and may be represented by equation 1, as shown below:

$$\frac{1-\alpha}{2}\left[1-\cos\left(\frac{\pi n}{w}\right)\right]^{\beta} \tag{1}$$

where w is the size of the aperture, n is the spatial frequency index, a is the adjustable pedestal parameter of the raising cosine function, and β is the adjustable power parameter of the raised cosine function. While the apodization function is described as a raising cosine function, any suitable function may be used.

FIG. 7C is an element directivity map 740 (e.g., an aperture diagram) according to aspects of the present disclosure. More specifically, FIG. 7C illustrates an element directivity map produced by applying the apodization function illustrated in the plot 720 of FIG. 7B to the ultrasound data (e.g., data resulting from the element directivity map 700) of FIG. 7A. As described with respect to the element directivity map 700 of FIG. 7A, the element directivity map 740 illustrates the relationship between transducer pairs (A-lines), where the x-axis indicates the transducer used to transmit ultrasound energy (e.g., the transmit (Tx) element) and the y-axis indicates the transducer element used to receive echoes associated with the transmitted ultrasound energy (e.g., the receive (Rx) element). Further, the element directivity map 740 is illustrated with respect to the 14-element transmit aperture and the 14-element receive aperture employed in the element directivity map 700 of FIG. 7A. Again, the elements within the illustrated aperture are numbered 1 through 14, where transducer 1 may be positioned at the first end of the aperture and transducer 14 may be positioned at the second end of the aperture. The element directivity map 740 further indicates an intensity level of received echoes associated with transmitted ultrasound energy (e.g., an intensity level of the A-lines) via grayscale color-coding. In particular, the whiter (e.g., brighter and/or lighter) regions of the element directivity map 700 indicate a relatively higher intensity level, while the darker (e.g., increasingly black) regions of the element directivity map indicate a relatively lower intensity level. Moreover, as described above, while the element directivity map 740 is illustrated with only one A-line for each reciprocal A-line pair (e.g., a reciprocal transducer, receiver element pair), embodiments are not limited thereto.

In comparison with the element directivity map 700 of FIG. 7A, the ultrasound data associated with off-center elements of the aperture has a relatively lower intensity within the element directivity map 740 of FIG. 7A. As an illustrative example, the intensity of the A-line associated with the first transmit element and the first receive element of the aperture (e.g., transducer 1) is reduced in the element directivity map 740 in comparison with the element directivity map 700, as illustrated by the darkened region. Moreover, the ultrasound energy associated with the center elements of the aperture is illustrated as having an increased or a relatively similar intensity within the element directivity map 700 and the element directivity map 740, as shown by the similar light (e.g., white) regions within FIGS. 7A and 7C. Further, each of the diagonals extending between the top right portion of the element directivity maps 700 and 740 to the bottom left portion of the element directivity maps 700 and 740 correspond to a respective spatial frequency. Thus, the differences between the element directivity map 700 and the element directivity map 740 thus demonstrate that application of the apodization function illustrated in the plot 720 to ultrasound energy associated with an aperture passes and/or emphasizes ultrasound data corresponding to center elements of the aperture (e.g., centered spatial frequencies) with respect to (e.g., and/or de-emphasizes) ultrasound data corresponding to off-center elements of the aperture (e.g., off-center spatial frequencies). De-emphasizing off-center spatial frequencies may suppress side lobe and grating lobe artifacts in image data and/or an ultrasound image generated based on the apodized ultrasound data. Accordingly, the operation 318 of FIG. 3 may produce ultrasound image data and/or an ultrasound image associated with reduced side lobe and grating lobe artifacts (e.g., reduced noise) in comparison with image data and/or an ultrasound image generated based on data that is not apodized, such as ultrasound data corresponding to the element directivity map 700 of FIG. 7A.

Turning back now to FIG. 3, the operation 318 may be performed by a beamformer, which may be included in the intraluminal imaging device 102, the PIM 104, and/or the processing system 106. For instance, the beamformer may perform a delay-and-sum operation on the data (e.g., RF data 310 and/or IQ data 316) to provide beamformed signals. In some embodiments, phase rotation may be performed along with the delay-and-sum operation on the IQ data 316 to produce beamformed data 320 with greater accuracy. Further, in some embodiments, the beamformer may include multiple stages of beamforming. Moreover, as described above, the data within the signal pathway 300 may include analog or digital signals. Thus, the beamformer may perform beamforming on the data in one or both of the analog or digital domain. Additionally or alternatively, the operation 318 may be performed by a processor circuit, such as processor circuit 210 of FIG. 2. In some embodiments, for example, a GPU may perform apodization on RF data 310 (e.g., filtered RF data) and/or IQ data 316. Moreover, performance of the operation 318 by a beamformer and/or a processor circuit may produce beamformed data 320, as further illustrated.

The signal pathway 300 may further include an envelope detection module 322. The envelope detection module 322 may be implemented as an envelope detector (e.g., a rectifier, a filter, and/or the like) that may output the envelope of the data within the signal pathway 300, such as the beamformed data 320. In addition to or in the alternative of the envelope detector, the envelope detection of the envelope detection may be performed at a beamformer, such as a beamformer employed to perform the operation 318. Additionally or alternatively, a GPU (e.g., a processor circuit 210) may be implemented to perform envelope detection or a portion thereof on the data within the signal pathway 300.

A time gain control module 324 (e.g., a time gain compensation module) of the signal pathway may be configured to apply gain to data within the signal pathway 300. In particular, the time gain control module 324 may be configured to apply gain to portions of the data based on a sampling time (e.g., a depth) associated with the portions of data. In some embodiments, for example, the time gain control module 324 may apply relatively greater gain to portions of the data with relatively greater sampling times and may apply relatively lower gain to portions of the data with relatively lower sampling times (e.g., in accordance with time-of-flight (TOF) adjustment). In this way, the time gain control module 324 may compensate for attenuation of ultrasound energy with increased depth through a medium, such as tissue. In some embodiments, a processor circuit, such as processor circuit 210 may implement the time gain control module 324. For instance, a GPU (e.g., a processor circuit 210) may be implemented to adjust the gain of the data within the signal pathway 300.

A scan conversion module 326 may perform scan conversion on the data within the signal pathway (e.g., image data) to provide an image 328 with a suitable display format. In an example, the image data may be in a polar coordinate and the scan conversion module 326 may convert the image data into Cartesian coordinates for display. In some embodiments, a processor circuit, such as processor circuit 210 of FIG. 2, may implement the scan conversion module 326. In some embodiments, for example, a GPU may perform scan conversion on the data.

The signal pathway 300 may output the image 328 (e.g., an ultrasound image) to a display 330 in communication with the signal pathway 300. The display 330 may be substantially similar to the monitor 108 of FIG. 1.

While the signal pathway 300 is illustrated and described herein as including a certain set of components and/or involving certain operations, embodiments are not limited thereto. To that end, additional components and/or operations may be included and/or components and/or operations may be omitted. For instance, the signal pathway 300 may additionally or alternatively include an ADC (e.g., involve analog-to-digital conversion), any suitable filter (e.g., a low pass filter, a high pass filter, a band pass filter, and/or the like), a buffer and/or memory device, which may temporarily store and/or duplicate data, and/or the like. Further, the signal pathway 300 may include a log compression module configured to perform log compression on the data (e.g., image data) within the signal pathway 300. In some embodiments, the log compression module may perform log compression on the data after the envelope detection is performed (e.g., via the envelope detection module 322). To that end, the log compression may be applied to the envelope of the data. In some embodiments, a processor circuit, such as processor circuit 210 of FIG. 2, may implement the log compression module. In some embodiments, for example, a GPU may perform log compression on the data within the signal pathway 300. Moreover, while the signal pathway 300 is illustrated in a particular order, one or more of the components and/or operations may be performed in a different order or may be performed in parallel. Further, the signal pathway 300 may be implemented to perform operations with respect to real-valued and/or complex-valued data. In this regard, in some embodiments, the signal pathway 300 may receive complex-valued data (e.g., IQ data) and may filter such data, which may be baseband data, with a low-pass filter. Moreover, while the filter shown in FIG. 4 is a real-valued filter, a complex filter, such as a complex low-pass filter, may be applied to this data. Similarly, the apodization associated with the operation 318 may be applied in the complex domain, which may involve performing phase rotation.

Figure 8:
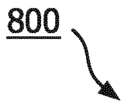
FIG. 8 is an ultrasound image, according to aspects of the present disclosure.
Figure 8:
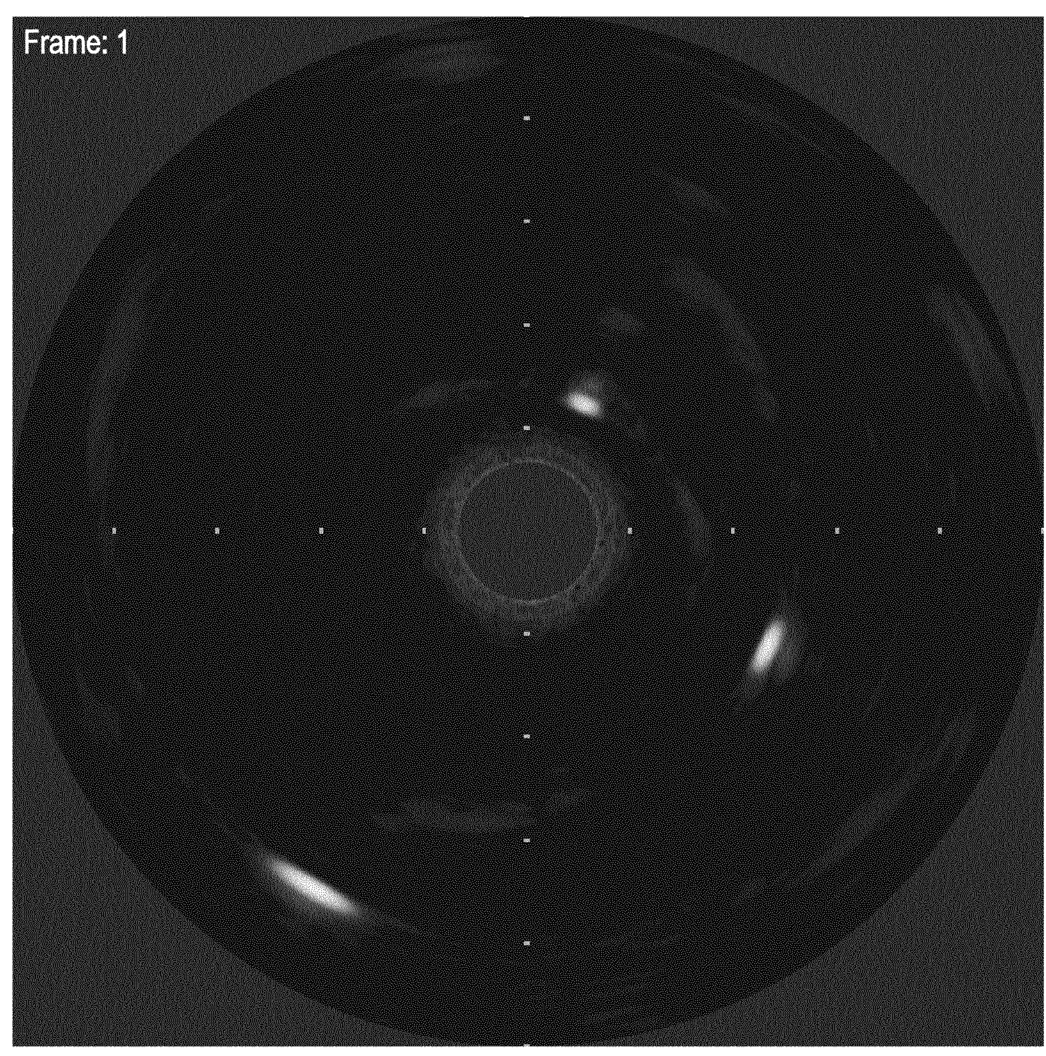

FIG. 8 illustrates an exemplary ultrasound image 800 (e.g., a B-mode ultrasound image) generated in accordance with the techniques described herein with respect to FIGS. 3-6 and 7A-C. In particular, the ultrasound image 800 may be generated based on performing a first filtering and a first apodization on ultrasound data. For instance, the ultrasound 800 may be generated based on applying a regular filter (e.g., via the bandpass filter 312) and performing a beamforming with regular apodization (e.g., at the beamforming with apodization operation 318) on the ultrasound data. To that end, the ultrasound image 800 may be produced by the signal pathway 300 of FIG. 3 and/or may correspond to the image 328 illustrated in FIG. 3.

Figure 9A:
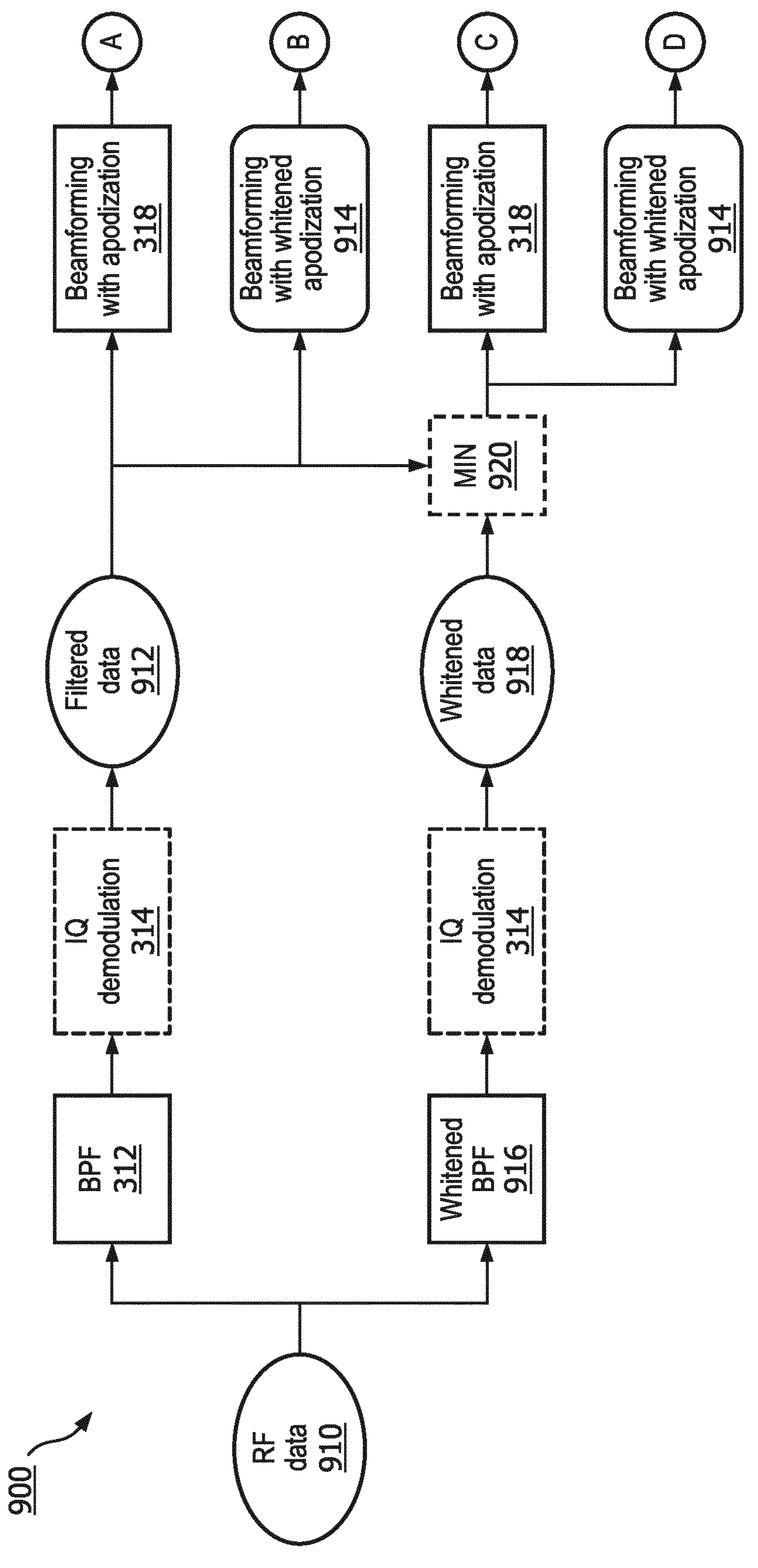
FIGS. 9A-9B illustrate a block diagram of a signal pathway for generating an ultrasound image, according to aspects of the present disclosure.
Figure 9B:
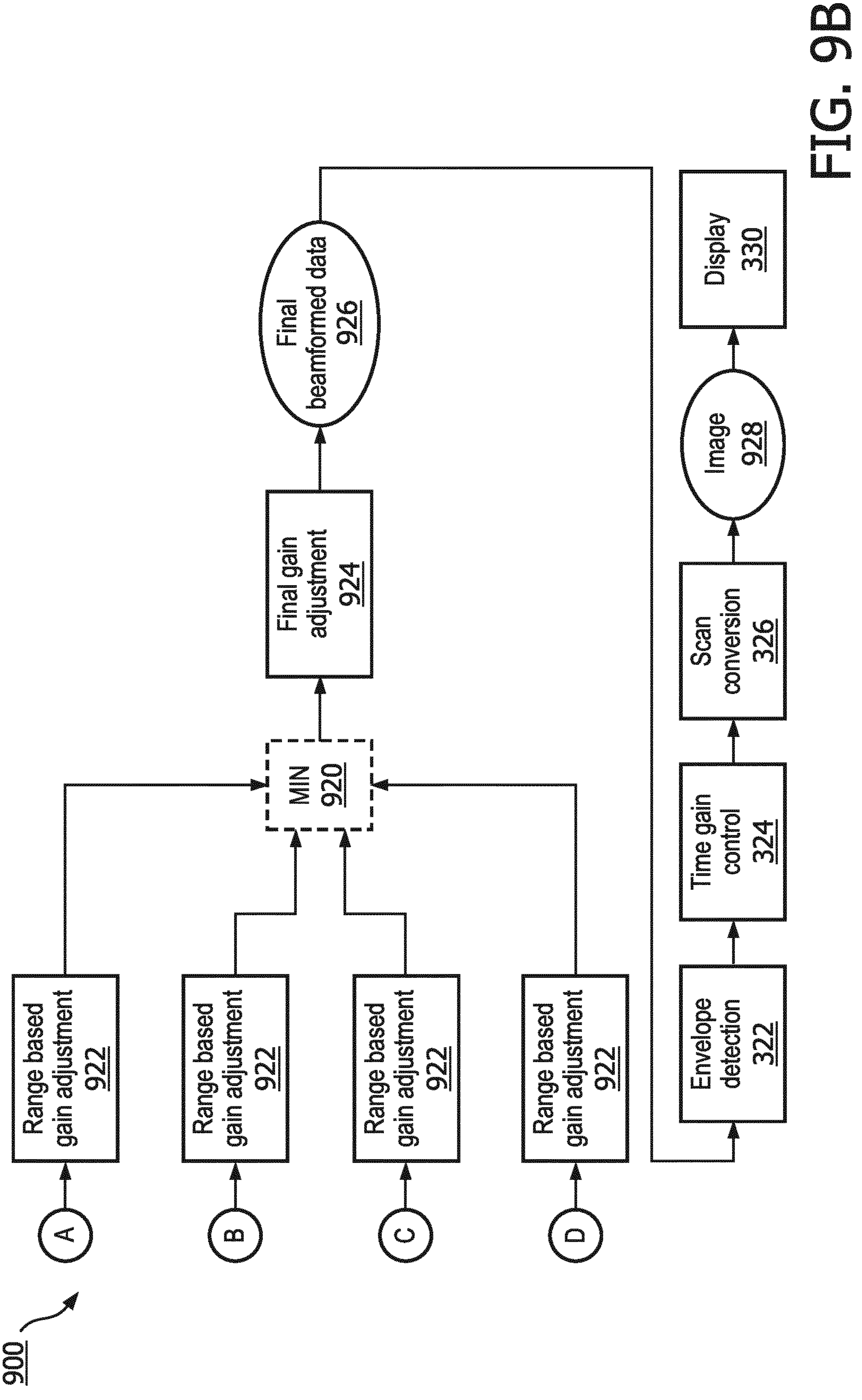

FIGS. 9A-9B illustrate a signal pathway 900 for generating an ultrasound image, according to aspects of the present disclosure. In particular, the signal pathway 900 may generate an ultrasound image and/or image data with a different resolution in comparison with an ultrasound image and/or image data, such as ultrasound image 800 (FIG. 8), generated in accordance with the signal pathway 300 illustrated in FIG. 3. More specifically, the image and/or image data generated by signal pathway 900 may have an axial and/or a lateral resolution exceeding a corresponding axial and/or lateral resolution of the image and/or image data generated by the signal pathway 300. The signal pathway 900 may be associated with a method, or process, for image generation. It will be understood that the elements of the signal pathway 900 may comprise computer program code or instructions executable by a processor circuit, such as the processor circuit 210 shown in FIG. 2. For example, in some embodiments, the elements of the signal pathway 900 comprise different processing (e.g., software) modules. In some embodiments, the elements of the signal pathway 900 comprise different hardware components.

In some embodiments, the components and/or operations of the signal pathway 900 are implemented by the intraluminal imaging device 102, the PIM 104, and/or the processing system 106 shown in FIG. 1. In particular, components of the signal pathway 900 may be implemented by a beamformer and/or a processor circuit, such as processor circuit 210, included in the intraluminal imaging device 102, the PIM 104, and/or the processing system 106. In some embodiments, for example, the components of the signal pathway 900 are distributed between the intraluminal imaging device 102, the PIM 104, and/or the processing system 106. Moreover, the components of the signal pathway 900 can be implemented via a combination of hardware and software components, and may be executed by the processor circuit 210 described above with respect to FIG. 2. For instance, in some embodiments, one or more components and/or operations of the signal pathway 900 can be executed by a GPU or an FPGA. Further, in some embodiments, the signal pathway 300 illustrated in FIG. 3 may be modified to produce the signal pathway 900 illustrated in FIGS. 9A-9B. In some embodiments, for example, the components and/or operations of the signal pathway 900 that are not illustrated within the signal pathway 300 may be implemented by a processor circuit (e.g., processor circuit 210) such that components and/or operations may be added and/or removed from the signal pathway 300 without making hardware changes to the ultrasound imaging system 100. In this way, the techniques described herein may be retrofitted to an existing ultrasound imaging system without costly additions and/or changes to hardware of the ultrasound imaging system.

At a high level, the signal pathway 900 is configured to generate an ultrasound image based on applying a first combination of filtering and a apodization to ultrasound data to generate first image data associated with a first resolution (e.g., a first axial and a first lateral resolution), applying a second combination of filtering and a apodization to the ultrasound image data to generate second image data associated with a second resolution (e.g., a second axial and a second lateral resolution), and generating an image based on the first image data and the second image data, wherein the image includes a third resolution (e.g., a third axial and a third lateral resolution). The image may be generated based on performing a minimum (MIN) operation on the first image data and the second image data, for example. In particular, the illustrated signal pathway 900 is configured to generate first image data A, second image data B, third image data C, fourth image data D using a combination of respective filters and apodization and generate an ultrasound image based on the first through fourth image data (A-D). While the signal pathway 900 is illustrated and described as including two types of filters and two types of apodization functions such that four sets of image data (e.g., image data A-D) are generated, it may be appreciated that any suitable number of filters, apodization functions, and/or sets of image data may be included in or generated by the signal pathway 900. To that end, embodiments described herein are intended to be exemplary and not limiting.

Generally speaking, the signal pathway 900 includes features similar to signal pathway 300 (FIG. 3) in many respects. For example, each of the signal pathway 300 and the signal pathway 900 include a bandpass filter (BPF) 312, a beamforming with apodization operation 318, an envelope detection module 322, a time gain control module 324, a scan conversion module 326, and a display 330. Accordingly, for sake of brevity, details of those components and/or operations will not be repeated here.

The signal pathway 900 may receive ultrasound data (e.g., ultrasound signals) based on received echoes associated with ultrasound energy transmitted by an array of acoustic elements (e.g., transducer array 124). The ultrasound data may include analog or digital data. Further, as illustrated, the ultrasound data may be radio-frequency (RF) data 910. As described in greater detail below, the RF data 910 may include ultrasound data associated with a single data acquisition or multiple data acquisitions (e.g., a single, common transmit aperture or separate transmit apertures). In this regard, the same RF data 910 may be input to separate processing pathways within the signal pathway 900 (e.g., processing pathways used to generate the image data A-D) or respective portions of the RF data 910 may be input to the separate processing pathways.

The first image data A may be generated by filtering the RF data 910 using the bandpass filter 312 (e.g., a first filter) and optionally demodulating the data using the IQ demodulation module 314 to produce the filtered data 912, which may be real or complex-valued based on whether the demodulation was performed. The first image data A may further be generated based on a first apodization performed via the beamforming with apodization operation 318. The components and/or operations of the signal pathway 900 involved in generating the first image data A are generally similar to components and/or operations of the signal pathway 300. Accordingly, for sake of brevity, details of those components and/or operations will not be repeated here. Further, an ultrasound image generated based on the first image data A (e.g., by performing envelope detection, applying time gain control, performing scan conversion, and/or the like on the first image data A) may resemble the ultrasound image 800, as described with respect to FIG. 8.

The second image data B may be generated by filtering the RF data 910 using the bandpass filter 312 (e.g., a first filter) and optionally demodulating the data using the IQ demodulation module 314 to produce the filtered data 912, as described with respect to the first image data A. Moreover, to produce the second image data B, a second apodization function may be applied to the filtered data 912. The second apodization function may be different than the first apodization. For instance, in some embodiments, the first apodization function used to generate the first image data A may be configured to emphasize center spatial frequencies (e.g., spatial frequencies associated with center elements of an aperture) and to de-emphasize off-center spatial frequencies (e.g., spatial frequencies associated with off-center and/or edge elements of an aperture). That is, for example, the first apodization function may correspond to regular apodization. The second apodization function may be configured to de-emphasize center spatial frequencies (e.g., spatial frequencies associated with center elements of an aperture) and to emphasize off-center spatial frequencies (e.g., spatial frequencies associated with off-center and/or edge elements of an aperture). In this regard, the second apodization function may be a whitened and/or whitening apodization function, as described in greater detail with respect to FIGS. 10A-C. To that end, the generation of the second image data B may involve a beamforming with whitened apodization operation 914, as illustrated. Moreover, while the first and second apodization functions are illustrated and described as a regular and a whitened apodization, respectively, embodiments are not limited thereto. In this regard, any suitable combination of apodization functions may be employed within the signal pathway 900.

In some embodiments, the beamforming with a whitened apodization operation 914 may involve the second apodization function (e.g., a whitened apodization function). In some embodiments, the beamforming with a whitened operation 914 may involve the use of a second aperture. The second aperture may be a different aperture in comparison with the aperture associated with the beamforming with apodization operation 318. In some embodiments, for example, the second aperture may larger than the first aperture. More specifically, the transmit aperture and/or the receive aperture associated with the second aperture may include a greater number of elements than the transmit aperture associated with the first aperture. As an illustrative example, the transmit aperture of the second aperture may include 20 transducer elements, while the transmit aperture of the second aperture may include 14 transducer elements. The receive aperture of the first and second apertures may include the same quantity or different quantities of transducer elements. For instance, in some embodiments, the receive aperture of both the first and second aperture may be 14 transducer elements. In some embodiments, the second aperture may be smaller than the first aperture. For instance, the second aperture may utilize fewer elements for transmission or reception of ultrasound data than the first aperture. Further, the first and second apertures may be obtained with a single, common data acquisition or separate data acquisitions. In this regard, the RF data 910 of FIG. 9A may correspond to the single acquisition or a first portion of the RF data 910 may correspond to a data acquisition associated with the first aperture and a second portion of the RF data 910 may correspond to a data acquisition associated with the second aperture.

Figures 10A, 10B, 10C:
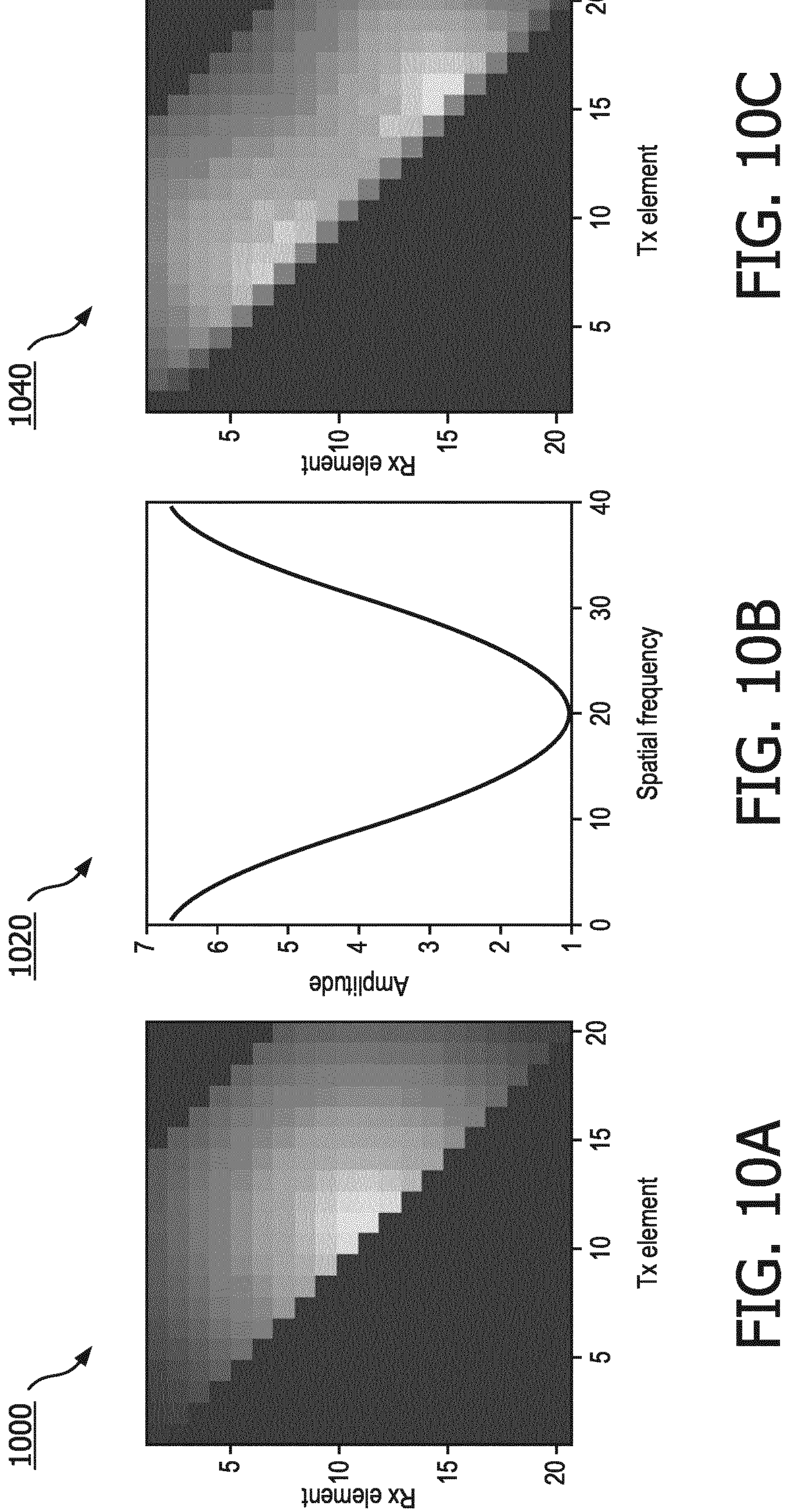
FIG. 10A is an element directivity map, according to aspects of the present disclosure.
FIG. 10B is a plot of an apodization function, according to aspects of the present disclosure, according to aspects of the present disclosure.
FIG. 10C is an element directivity map, according to aspects of the present disclosure.

With reference now to FIG. 10A, an element directivity map 1000 (e.g., an aperture diagram) according to aspects of the present disclosure is illustrated. The element directivity map 1000 is illustrated with respect to an exemplary aperture that uses a 20-element transmit aperture and a 14-element receive aperture. The elements within the illustrated aperture are numbered 1 through 20, where transducer 1 may be positioned at a first end of the aperture and transducer 20 may be positioned at a second end of the aperture. As described with respect to FIGS. 7A and 7C, element directivity map 1000 indicates intensities of ultrasound data (e.g., ultrasound signals) via grayscale color-coding. In particular, the whiter (e.g., brighter and/or lighter) regions of the element directivity map 1000 indicate a relatively higher intensity level, while the darker (e.g., increasingly black) regions of the element directivity map 1000 indicate a relatively lower intensity level. In this regard, the element directivity map 1000 shows that an intensity of ultrasound data associated with groupings of transmit and receive transducer elements within the center of an aperture is greater than an intensity of ultrasound data associated with groupings of transmit and receive transducer elements that are off-center.

As further illustrated, the shape of the element directivity map 1000 corresponds to the use of transmit elements 20 with the use of a respective set of 14 receive elements of a corresponding receive aperture (e.g., sub-aperture beamforming). For instance, for a first transmission, each of the 20 transmit elements may fire and a first subset of the elements, such as elements 1-14, may be used for reception of ultrasound energy, for a second transmission, each of the 20 transmit elements may fire and a second subset of the elements, such as elements 2-15, may be used for reception of ultrasound energy, and so on. Because the receive aperture for each transmission uses fewer transducer elements than the transmit aperture, the top right portion of the element directivity map 1000 lacks intensity level information. Moreover, the element directivity map 1000 is illustrated with only one A-line for each reciprocal A-line pair (e.g., a reciprocal transducer, receiver element pair), as described above with reference to FIGS. 7A-7C. In some embodiments, A-line data may be obtained and/or displayed within the element directivity map 1000 for each A-line pair of the aperture.

FIG. 10B is a plot 1020 of an apodization function according to aspects of the present disclosure. As illustrated, an x-axis of the plot 1020 is spatial frequency in arbitrary units, and a y-axis of the plot 1020 is amplitude in arbitrary units. The plot 1020 illustrates an apodization function (e.g., a whitened apodization function) that may be applied to ultrasound data, such as filtered data 912, in accordance the beamforming with whitened apodization operation 914 of FIG. 9. In particular, the plot 1020 illustrates an apodization function configured to emphasize ultrasound data corresponding to off-center and/or edge elements (e.g., transducer elements) of the aperture and to de-emphasize ultrasound data corresponding to center elements of the aperture. In this regard, the illustrated apodization function is configured to emphasize a spatial frequency corresponding to the off-center and/or edge elements of the aperture and to de-emphasize the spatial frequencies corresponding to the center elements of the aperture, as shown by the plot 1020.

A non-limiting example of an apodization function configured to emphasize ultrasound data corresponding to center elements of the aperture and to de-emphasize ultrasound data corresponding to off-center elements of the aperture (e.g., a whitened apodization function) is an inversed Hann window, which is illustrated in the plot 1020 and may be represented by equation 2, as shown below:

$$1-\alpha\cos^2\left(\frac{\pi n}{2w+1}\right) \quad (2)$$

where w is the size of the aperture, n is the spatial frequency index, α is the adjustable Hann function normalizer. In some embodiments, the adjustable Hann function normalizer can be varied with respect to a depth of the A-line, which may modify the aggressiveness of the whitening function at different depths. That is, for example, the whitened apodization function may be employed as a depth-dependent function with respect to the ultrasound data. Further, while the whitened and/or second apodization function is described as an inversed Hann window, any suitable function may be used. In particular, while the first and second apodization functions are illustrated and described as a regular and a whitened apodization, respectively, embodiments are not limited thereto. In this regard, any two suitable apodization functions may be employed within the signal pathway 900 of FIG. 9.

FIG. 10C is an element directivity map 1040 (e.g., an aperture diagram) according to aspects of the present disclosure. More specifically, FIG. 10C illustrates an element directivity map produced by applying the apodization function illustrated in the plot 1020 of FIG. 10B to the ultrasound data (e.g., to ultrasound data corresponding to the element directivity map 1000) of FIG. 10A. As described with respect to FIG. 10A, the element directivity map 1040 is illustrated with respect to the exemplary 20-element transmit aperture and the 14-element receive aperture. Again, the elements within the illustrated aperture are numbered 1 through 20, where transducer 1 may be positioned at the first end of the aperture and transducer 20 may be positioned at the second end of the aperture. The element directivity map 1040 further indicates an intensity level of received echoes associated with transmitted ultrasound energy (e.g., an intensity level of the A-lines) via grayscale color-coding. In particular, the whiter (e.g., brighter and/or lighter) regions of the element directivity map 1040 indicate a relatively higher intensity level, while the darker (e.g., increasingly black) regions of the element directivity map indicate a relatively lower intensity level.

As similarly described above, the shape of the element directivity map 1040 corresponds to the use of transmit elements 1-20 (e.g., the 20-element transmit aperture) with the use of a respective set of 14 receive elements of a corresponding receive aperture (e.g., sub-aperture beamforming). Moreover, the element directivity map 1040 is illustrated with only one A-line for each reciprocal A-line pair (e.g., a reciprocal transducer, receiver element pair), as described above with reference to FIGS. 7A-7C. In some embodiments, A-line data may be obtained and/or displayed within the element directivity map 1040 for each A-line pair of the aperture.

In comparison with the element directivity map 1000 of FIG. 10A, the ultrasound data associated with off-center elements of the aperture has a relatively higher intensity within the element directivity map 1040 of FIG. 10C. As an illustrative example, the intensity of the A-line associated with transmit element 20 and the receive element 20 of the aperture is increased in the element directivity map 1040 in comparison with the element directivity map 1000, as illustrated by the lightened region. Moreover, the ultrasound energy associated with the center elements of the aperture is shown as having a relatively lower intensity within the element directivity map 1040 in comparison with the element directivity map 1000, as shown by the relatively darker regions corresponding to the center elements within FIG. 10C. Further, each of the diagonals extending between the top right portion of the element directivity maps 1000 and 1040 to the bottom left portion of the element directivity maps 1000 and 1040 correspond to a respective spatial frequency. Thus, the differences between the element directivity map 1000 and the element directivity map 1040 thus demonstrate that application of the apodization function illustrated in the plot 1020 to ultrasound energy associated with an aperture passes and/or emphasizes (e.g., amplifies) ultrasound data corresponding to off-center elements of the aperture (e.g., off-centered spatial frequencies) and de-emphasizes ultrasound data corresponding to center elements of the aperture (e.g., center spatial frequencies). De-emphasizing center spatial frequencies and emphasizing off-center spatial frequencies may increase lateral resolution of an ultrasound image in comparison with an ultrasound image generated where the center spatial frequencies are emphasized and the off-center spatial frequencies are de-emphasized. Accordingly, the operation 914 of FIG. 9 may produce ultrasound image data that produces an ultrasound image with increased lateral image resolution in comparison with an ultrasound image generated based on data produced by the operation 318 of FIG. 3.

Figure 11B:
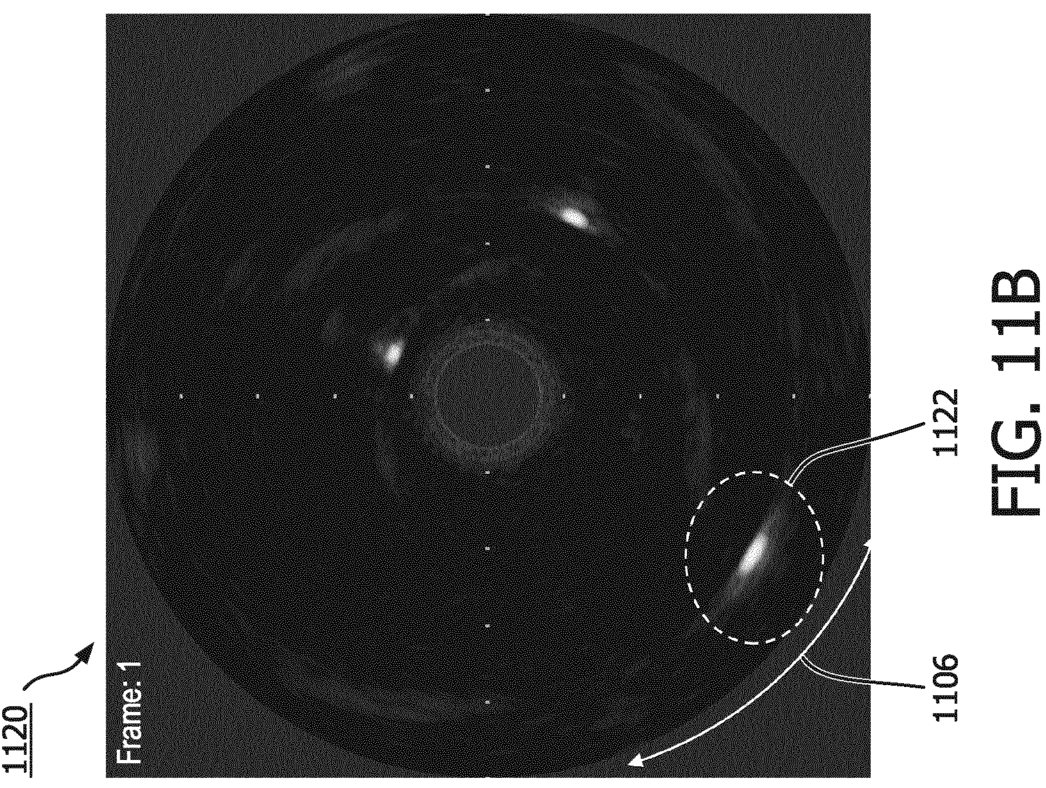
FIGS. 11A-11B illustrate ultrasound images, according to aspects of the present disclosure.
Figure 11A:
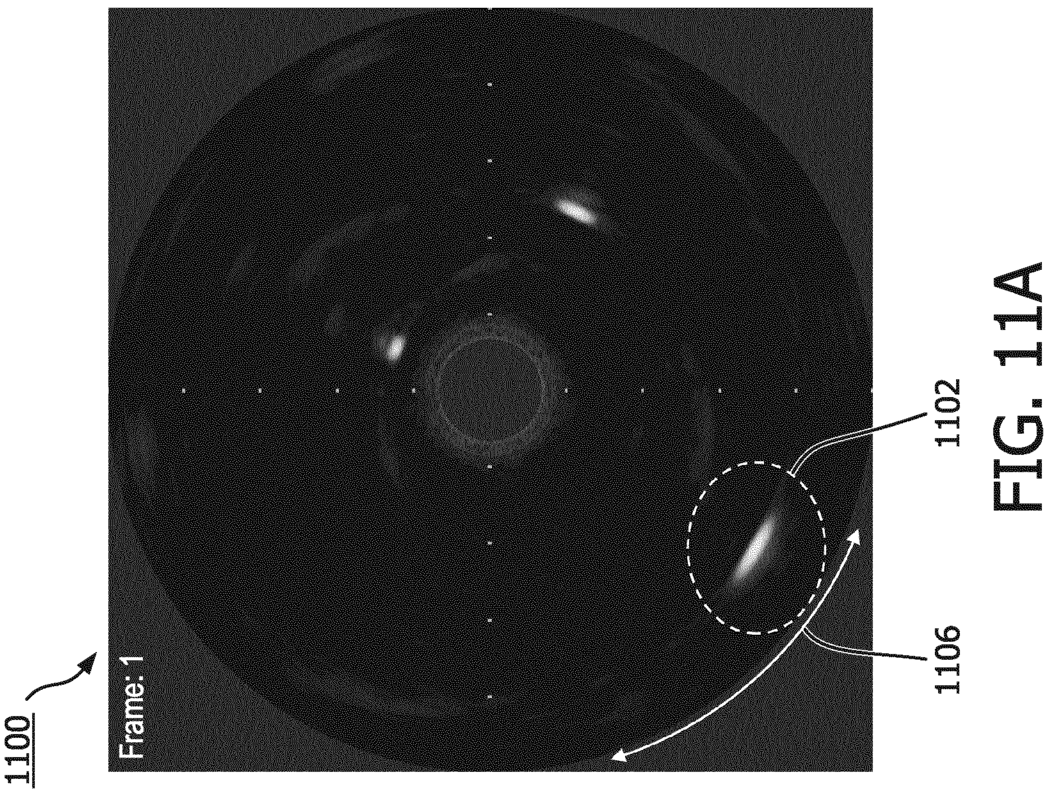

FIGS. 11A-11B illustrate exemplary ultrasound images (e.g., B-mode ultrasound images) of a common target generated in accordance with the techniques described herein. FIGS. 11A-11B facilitate a comparison of first image data A of FIG. 9A with second image data B of FIG. 9A. In particular, FIGS. 11A-B facilitate a comparison of an ultrasound image generated based on the first image data A of FIG. 9A with an ultrasound image generated based on the second image data B of FIG. 9A. In this regard, FIG. 11A illustrates an ultrasound image 1100 that is identical to the ultrasound image 800 of FIG. 8 and may be generated based on processing (e.g., envelope detection, time gain control, scan conversion, and/or the like) of the first image data A of FIGS. 9A-9B. To that end, the ultrasound image 1100 may be generated by the signal pathway 300 of FIG. 3. FIG. 11B illustrates an ultrasound image 1120 generated based on processing (e.g., envelope detection, time gain control, scan conversion, and/or the like) of the second image data B of FIGS. 9A-9B. That is, for example, the ultrasound image 1120 may be generated based on performing a first filtering and a second apodization on ultrasound data. For instance, the ultrasound 1120 may be generated based on applying a bandpass filter (e.g., via the bandpass filter 312) and performing a beamforming with whitened apodization (e.g., at the beamforming with whitened apodization operation 914) on the ultrasound data. Moreover, while the ultrasound image 1100 is generated with a 14-element transmit aperture and a 14-element receive aperture, the ultrasound image 1120 is generated with a 20-element transmit aperture and a 14-element receive aperture.

In comparison with the ultrasound image 1100, the ultrasound image 1120 has a greater lateral resolution. For instance, the region 1122 of the ultrasound image 1120 has sharper edges along a lateral axis 1106 than the corresponding region 1102 of the ultrasound image 1100. In further comparison with the ultrasound image 1100, the ultrasound image 1120 has increased side and/or grating lobes (e.g., image artifacts). In some embodiments, the side and/or grating lobes may be minimized and/or reduced by tuning characteristics of the second apodization function, such as the amount of emphasis or de-emphasis (e.g., weights) the function applies to different spatial frequencies. Tuning such characteristics may also alter the lateral resolution in the resulting image data.

Turning back now to FIG. 9A, the signal pathway 900 may generate third image data C by performing a second filtering and the first apodization on ultrasound data (e.g., the RF data 910). As described with respect to the first image data A, the first apodization may be a beamforming with regular apodization, which may be performed via the beamforming with apodization operation 318. In particular, the first apodization may correspond to applying an apodization configured to emphasize (e.g., amplify) ultrasound data corresponding to center elements of an aperture and to de-emphasize ultrasound data corresponding to off-center elements of the aperture, where the aperture may include a transmit aperture and a receive aperture that utilize a first quantity of transducer elements (e.g., a 14-element transmit aperture and a 14-element receive aperture). The second filtering may be different than the first filtering described with respect to the first image data A and the second image data B (e.g., with respect to the bandpass filter 312). For instance, in some embodiments, the first filter used to generate the first image data A and the second image data B may be configured to emphasize center frequencies and to de-emphasize off-center frequencies. That is, for example, the first filtering may correspond to regular filtering, which may be performed at the bandpass filter 312. The second filtering may be configured to de-emphasize center frequencies and to emphasize off-center frequencies. In this regard, the second filtering may be a whitened and/or whitening filtering, as described in greater detail with respect to FIG. 12. To that end, the generation of the third image data C may involve a filtering with a second filter. More specifically, the signal pathway 900 may include a second filter, such as the illustrated whitened bandpass filter (BPF) 916. Moreover, while the first and second filtering are illustrated and described as a regular and a whitened filtering, respectively, embodiments are not limited thereto. In this regard, any suitable filtering may be employed within the signal pathway 900.

Figure 12:
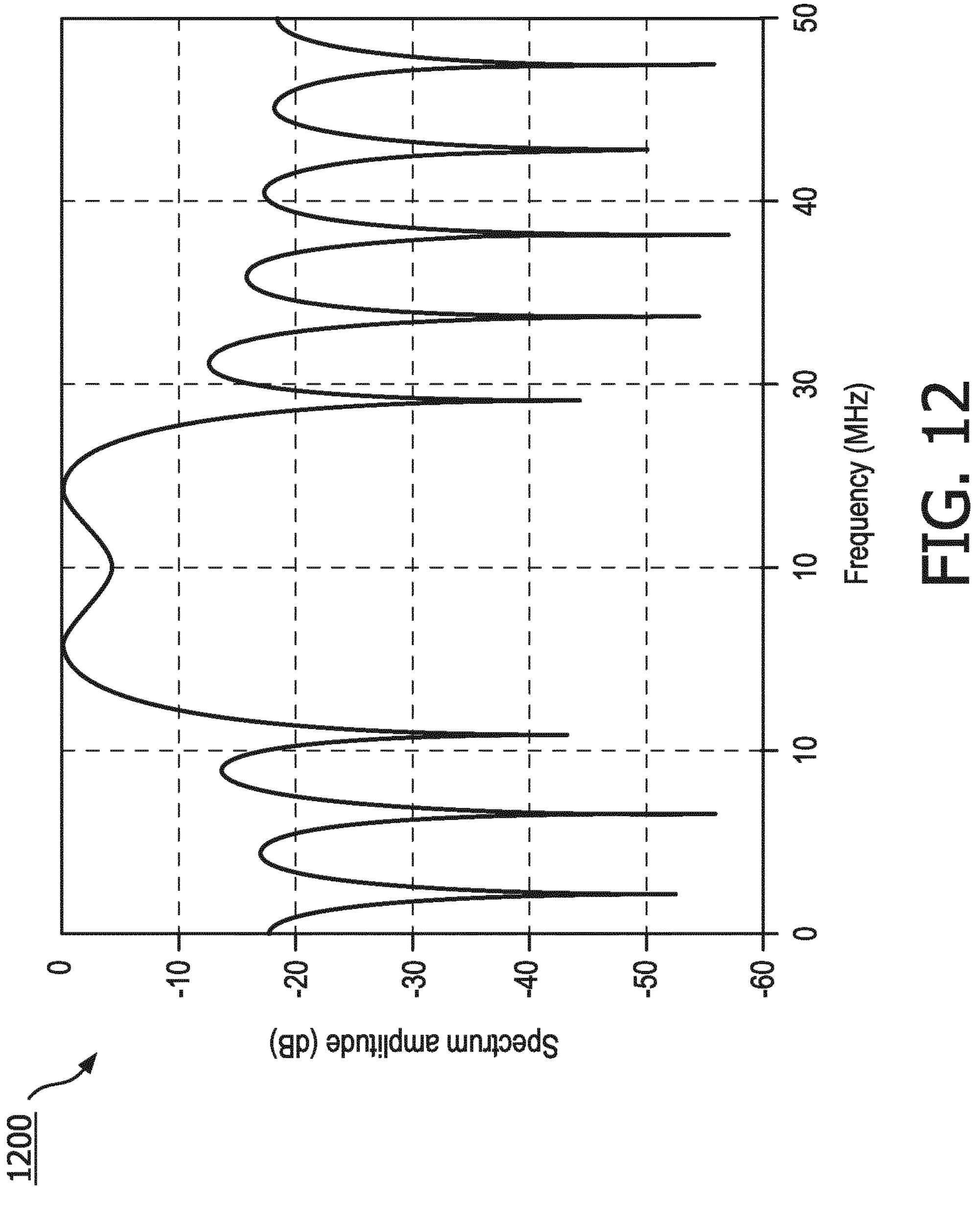
FIG. 12 is a plot of a frequency response of a filter, according to aspects of the present disclosure.

With reference now to FIG. 12, a plot 1200 of a frequency response of a whitening bandpass filter, such as the whitened bandpass filter 916 of FIG. 9A, is illustrated. As shown, the frequency response is plotted against spectrum amplitude in decibels (dB) on a y-axis of the plot 1200 and frequency in megahertz (MHz) on an x-axis of the plot 1200. As further shown, a filter with the plotted response is configured to de-emphasize frequencies about a center frequency and to emphasize off-center frequencies. In particular, the filter is configured to de-emphasize frequencies at approximately 20 MHz and emphasize frequencies less than and greater than approximately 20 MHz, such as approximately 15 MHz and approximately 25 MHz. That is, for example, the filter is configured to pass the frequencies at approximately 15 MHz and approximately 25 MHz such that these frequencies are emphasized with respect to the frequencies at approximately 20 MHz. In some embodiments, the filter may be configured to de-emphasize a center frequency associated with ultrasound data input to the filter, such as RF data 910. That is, for example, the center frequency de-emphasized by the filter may be the center frequency of the transducer array 124.

With reference to FIG. 9A, the whitened bandpass filter 916 may exhibit a frequency response similar to the frequency response shown in the plot 1200 of FIG. 12. The whitened bandpass filter 916 may be implemented as an analog or a digital filter. In that regard, the whitened bandpass filter 916 may be implemented as any suitable filter, such as a finite impulse response (FIR) filter, an infinite impulse response (IIR) filter, and/or the like. Moreover, while the signal pathway 900 is illustrated as including the whitened bandpass filter 916, it may be appreciated that any suitable filter, such as a whitened low pass filter, a whitened high pass filter, and/or the like may be additionally or alternatively included in the whitened bandpass filter 916. As further shown, the whitened bandpass filter 916 may output whitened data 918 and/or may output data that is demodulated at the optional IQ demodulation module 314 to generate the whitened data 918.

Further, in some embodiments, a combination of the first filtering (e.g., filtering applied by the bandpass filter 312) and the second filtering (e.g., filtering applied by the whitened bandpass filter 916) may be applied to ultrasound signals (e.g., the RF data 910). In some embodiments, for example, depth-dependent filtering may be applied to the ultrasound signals. To that end, different filtering may be applied to different portions of the ultrasound signals based on a depth associated with the respective portions. An illustrative example of a scheme 1300 for depth dependent filtering is shown in FIG. 13.

Figure 13:
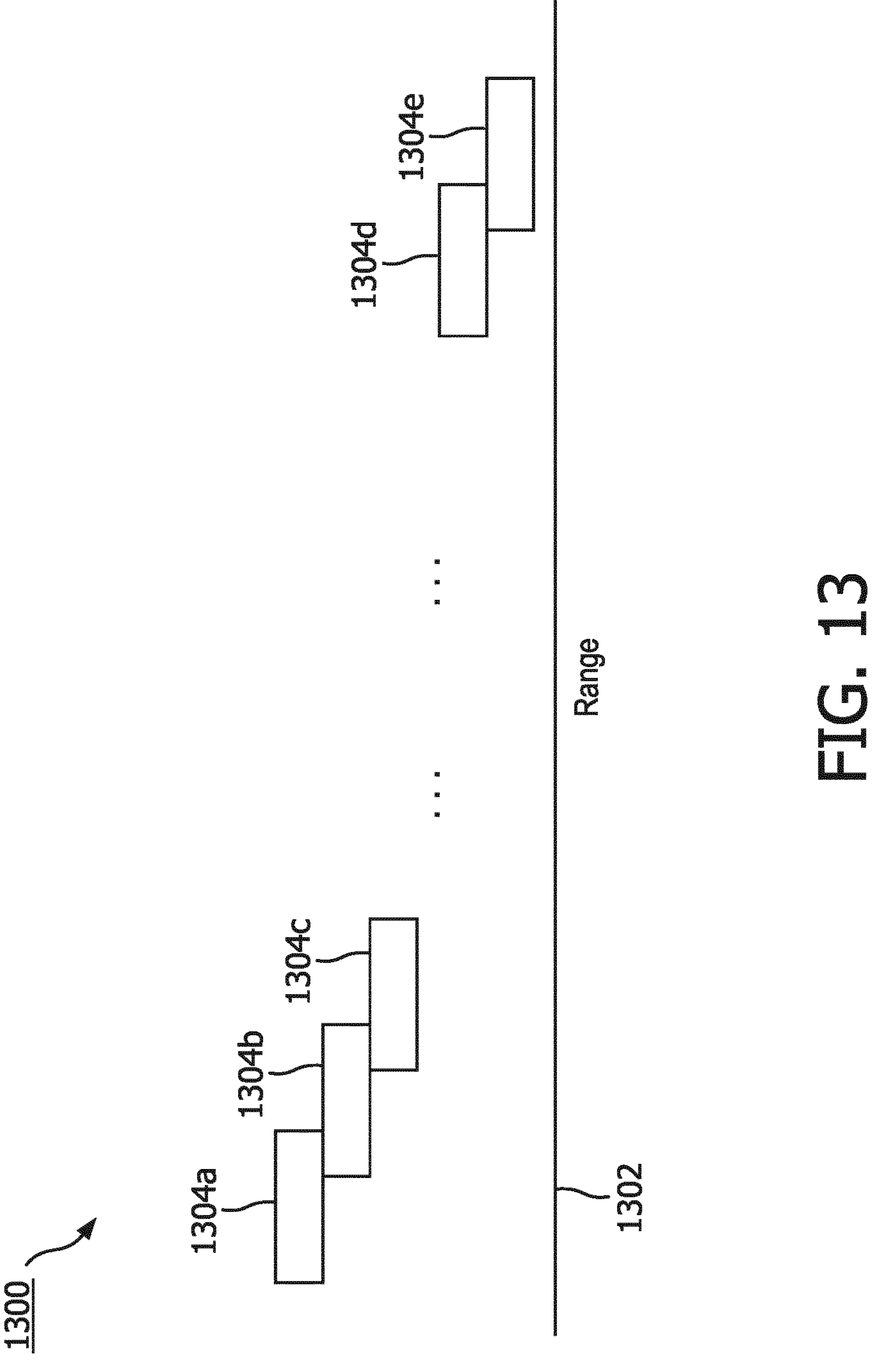
FIG. 13 illustrates a scheme for depth-dependent filtering, according to aspects of the present disclosure.

FIG. 13 illustrates a range 1302 (e.g., depth) of an A-line (e.g., an ultrasound signal associated with received echoes), where the range (e.g., depth) of the A-line increases from left to right. As illustrated the range 1302 of the A-line is shown as segmented into several overlapping windows 1304. For an A-line having a length of a particular quantity of samples, each of the windows 1304 may include a certain subset of the samples and may overlap other windows 1304 by a quantity of samples. For instance, an A-line with a length of 1320 samples may be segmented into 24 windows 1304. Each of these windows 1304 may contain 55 samples and may overlap another window 1304 by 20 samples.

In some embodiments the depth-dependent filtering scheme 1300 may involve applying a regular filter (e.g., a regular bandpass filter, such as the bandpass filter 312) to a first set of windows of the range 1302 (e.g., to samples within a subset of the range 1302). More specifically, the regular filter may be applied to one or more windows 1304 at the shallow end of the range 1302. In the illustrated embodiment, the regular filter is applied to the first window 1304*a* (e.g., the shallowest window), as shown by the first fill pattern of the first window 1304*a*. By applying the regular filter to one or more windows 1304 at the shallow end of the range 1302, such as the first window 1304*a*, a ringdown (e.g., Gibbs ringing) artifact may be minimized in an ultrasound image generated based on the depth-dependent filtered data.

In some embodiments, the remaining windows 1304 within the range 1302 (e.g., 1304*b-e*) may be filtered according to one or more whitened filters. For instance, the windows 1304*b-e* may be filtered by the whitened bandpass filter 916 of FIG. 9A and/or a filter exhibiting the frequency response shown in FIG. 12. Further, in some embodiments, the same whitened filter may be applied to each of the remaining windows 1304 (e.g., 1304*b-e*), as illustrated by the second fill pattern shared by the windows 1304*b-e*. In some embodiments, different filters and/or filters with different properties may be applied to the remaining windows 1304. For example, a first whitened filter, which may apply a first gain to frequency components of an ultrasound signal, may be applied to a first subset of the remaining windows 1304. Further, a second whitened filter, which may apply a different, second gain to the frequency components of the ultrasound signal may be applied to a different, second subset of the remaining windows 1304. In this way, characteristics of filters applied to the windows 1304 may be tuned for application to a particular window 1304.

In some embodiments, overlapping portions of filtered windows 1304 may be averaged or otherwise weighted and/or combined. For instance, the overlapping set of samples included in the first window 1304*a* and the second window 1034*b* may be averaged and/or combined such that an effect of the filter applied to a portion of first window 1304*a* (e.g., the regular filter) containing the overlapped samples is combined with an effect of the filter applied to a portion of the second window 1304*b* (e.g., a whitened filter) containing the overlapped samples.

With reference now to FIG. 9A, the signal pathway 900 may optionally include and/or use (e.g., as indicated by dashed lines) a minimum operation module 920. The minimum operation module 920 may combine the filtered data 912 with the whitened data 918 based on a minimum operation, such as a minimum intensity projection (MIP). For instance, for each portion of the filtered data and corresponding portion of the whitened data (e.g., for data corresponding to each pixel location within the filtered data and the whitened data), the minimum operation module 920 may take a minimum value from among a value of the portion within the filtered data and a value of the corresponding portion within the whitened data. As such, the minimum operation module 920 may suppress and/or minimize an artifact in an ultrasound image resulting from the whitened data 918. In particular, the minimum operation module 920 may suppress Gibbs ringing within such an ultrasound image. In some embodiments, a processor circuit, such as processor circuit 210 of FIG. 2, may implement the minimum operation module 920. In some embodiments, for example, a GPU may perform a minimum operation using the filtered data 912 and the whitened data 918. Further, while the module 920 and/or the combination of image data is described herein with respect to a minimum operation, such as a minimum intensity projection, embodiments are not limited thereto. In this regard, image data may be combined using linear combination, such as a linear combination based on sorting, or any other suitable techniques. In some embodiments, for example, image data may be incoherently combined via linear combination to reduce artifacts in a resulting image. Additionally or alternatively, first and second image data, such as filtered data and whitened data, may be combined by applying a first gain to the first image data and a different, second gain to the second image data before summing the first and second image data.

As further illustrated by FIG. 9A, the third image data C may be generated based on beamforming and apodizing, with a first apodization function, (e.g., via the beamforming with apodization operation 318) the output of the minimum operation module 920. Additionally or alternatively, the third image data C may be generated based on beamforming and apodizing, with the first apodization function, the whitened data 918 directly. That is, for example, the minimum operation module 920 may optionally be included in the signal pathway 900.

Figure 14B:
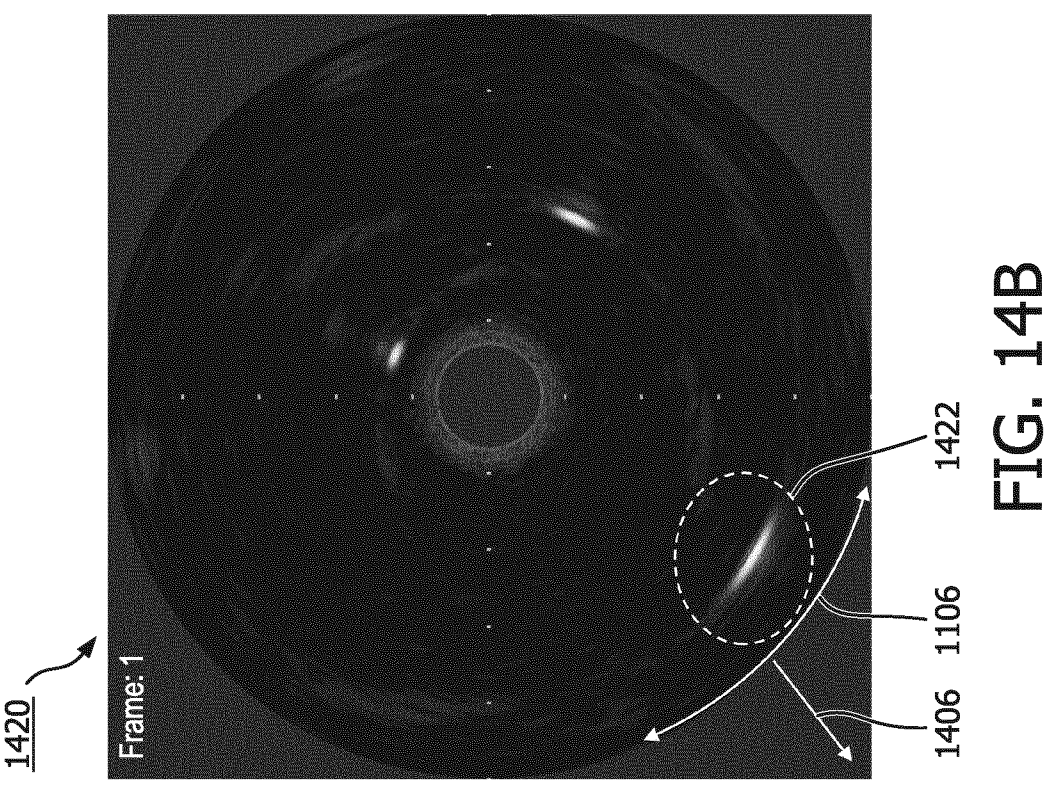
FIGS. 14A-14B illustrate ultrasound images, according to aspects of the present disclosure.
Figure 14A:
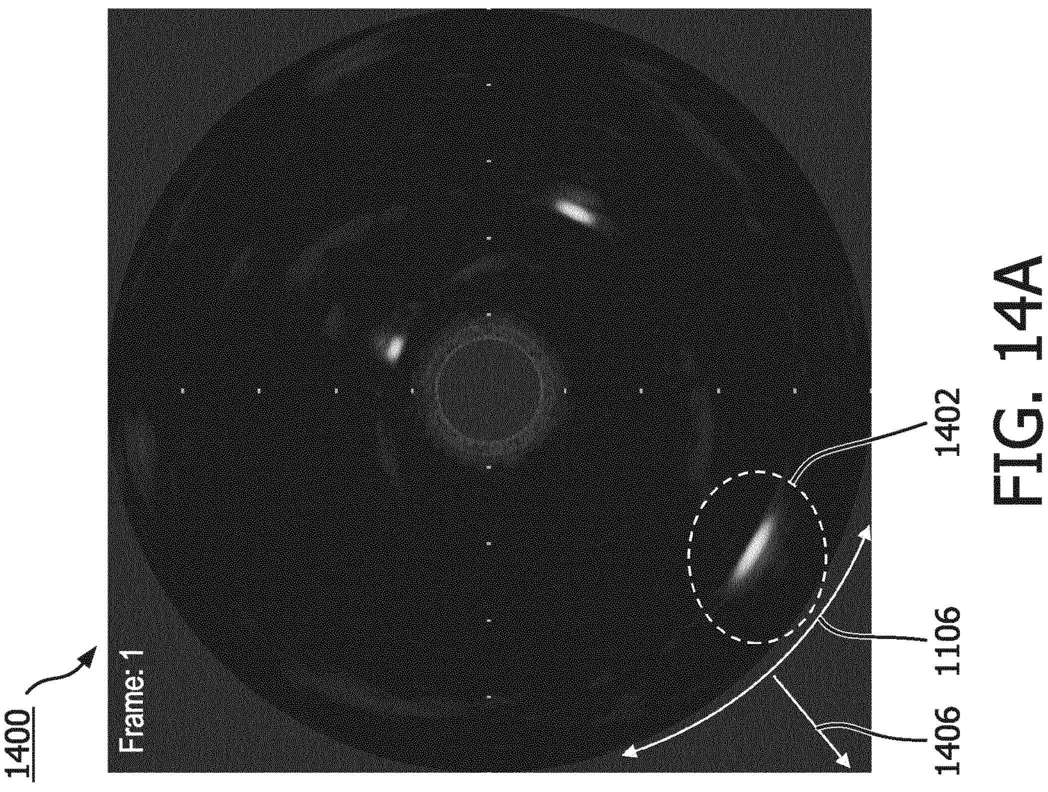

FIGS. 14A-14B illustrate exemplary ultrasound images (e.g., B-mode ultrasound images) of a common target generated in accordance with the techniques described herein. FIGS. 14A-14B facilitate a comparison of image data A of FIG. 9A with image data C of FIG. 9A. In particular, FIGS. 14A-14B facilitate a comparison of an ultrasound image generated based on the first image data A of FIG. 9A with an ultrasound image generated based on the third image data C of FIG. 9A. In this regard, FIG. 14A illustrates an ultrasound image 1400 that is identical to the ultrasound image 800 of FIG. 8 and the ultrasound image 1100 of FIG. 11A and may be generated based on processing (e.g., envelope detection, time gain control, scan conversion, and/or the like) of the first image data A of FIGS. 9A-9B. To that end, the ultrasound image 1400 may be generated by the signal pathway 300 of FIG. 3. FIG. 14B illustrates an ultrasound image 1420 generated based on processing (e.g., envelope detection, time gain control, scan conversion, and/or the like) of the third image data C of FIGS. 9A-9B. That is, for example, the ultrasound image 1420 may be generated based on performing a second filtering and a first apodization on ultrasound data. For instance, the ultrasound image 1420 may be generated based on applying a whitened bandpass filter (e.g., via the whitened bandpass filter 916) and performing a beamforming with regular apodization (e.g., at the beamforming with apodization operation 318) on the ultrasound data. The ultrasound image 1420 is further generated based on performing a minimum operation (e.g., via the minimum operation module 920) on the ultrasound data. In particular, the ultrasound image 1420 is generated based on performing a minimum intensity projection of first filtered ultrasound data (e.g., filtered data 912) and second filtered ultrasound data (e.g., whitened data 918). Moreover, each of the ultrasound image 1400 and the ultrasound image 1400 is generated with a 14-element transmit aperture and a 14-element receive aperture.

In comparison with the ultrasound image 1400, the ultrasound image 1420 has a greater axial resolution. The difference in axial resolution may be observed with respect to region 1402 of the ultrasound image 1400 and the corresponding region 1422 of the ultrasound image 1420. For instance, the region 1422 of the ultrasound image 1420 has sharper edges along an axial axis 1406 than the corresponding region 1402 of the ultrasound image 1400. In further comparison with the image 1400, the image 1420 has greater Gibbs ringing (e.g., an image artifact), which appears as extra halos within the region 1422. As described above, the effect of the Gibbs ringing may be tuned using depth-dependent filtering and/or adjusting characteristics of the whitened filter. Such tuning may also alter the axial resolution of a resulting ultrasound image.

Turning back now to FIG. 9A, the signal pathway 900 may generate fourth image data D by performing the second filtering and the second apodization on ultrasound data (e.g., the RF data 910). As described above, the second filtering may be different than the first filtering described with respect to the first image data A and the second image data B (e.g., with respect to the bandpass filter 312). For instance, in some embodiments, the first filtering may pass center frequencies such that the center frequencies are emphasized with respect to off-center frequencies, which may be de-emphasized by the first filtering, while the second filtering may pass off-center frequencies such that the off-center frequencies are emphasized with respect to center frequencies, which may be de-emphasized by the second filtering. That is, for example, the first filtering may correspond to regular filtering, which may be performed at the bandpass filter 312, and the second filtering be a whitened and/or whitening filtering, which may be performed at the whitened bandpass filter 916. As further described above, the second apodization may be a beamforming with whitened apodization, which may be performed via the beamforming with whitened apodization operation 914. In particular, the second apodization may correspond to applying an apodization configured to emphasize (e.g., amplify) ultrasound data corresponding to off-center elements of an aperture and to de-emphasize ultrasound data corresponding to center elements of the aperture, where the aperture may be different than an aperture used in conjunction with the beamforming with apodization operation 318. In particular, the second apodization may be associated with a transmit aperture with a greater number of elements than the first apodization, such as an aperture with a 20-element transmit aperture and a 14-element receive aperture.

In some embodiments, in addition to the second filtering and the second apodization, the fourth image data D may optionally be generated based on a minimum operation, such as an operation performed via minimum operation module 920. For instance, as described above with respect to the third image data C, the fourth image data D may be generated based on a combination of the filtered data 912 and the whitened data 918 via the minimum operation module 920. Again, while the module 920 and/or the combination of image data is described with respect to a minimum operation, image data may be generated and/or combined using linear combination or any other suitable techniques.

As illustrated and described with respect to FIG. 11B, use of the second apodization may produce image data (e.g., second image data B) with improved lateral resolution. As illustrated and described with respect to FIG. 14B, use of the second filtering may produce image data (e.g., third image data D) with improved axial resolution. With respect now to fourth image data D, performing the second filtering and the second apodization on ultrasound data may generate image data with both improved lateral resolution and improved axial resolution.

Figure 15B:
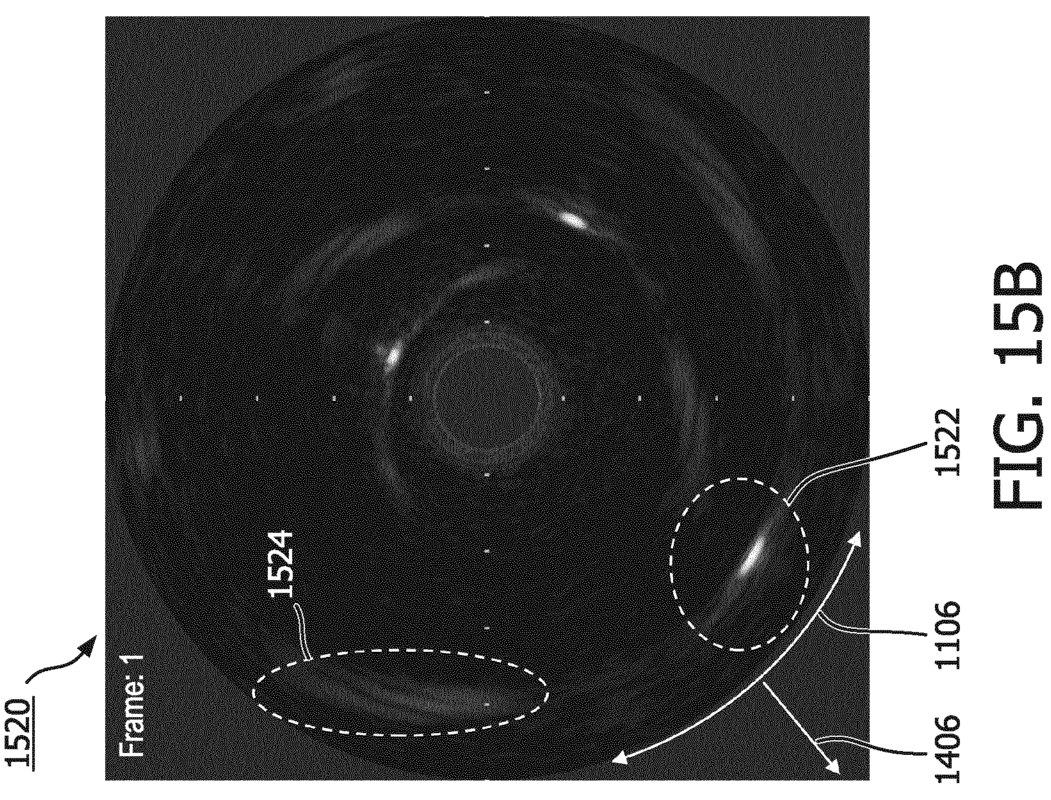
FIGS. 15A-15B illustrate ultrasound images, according to aspects of the present disclosure.
Figure 15A:
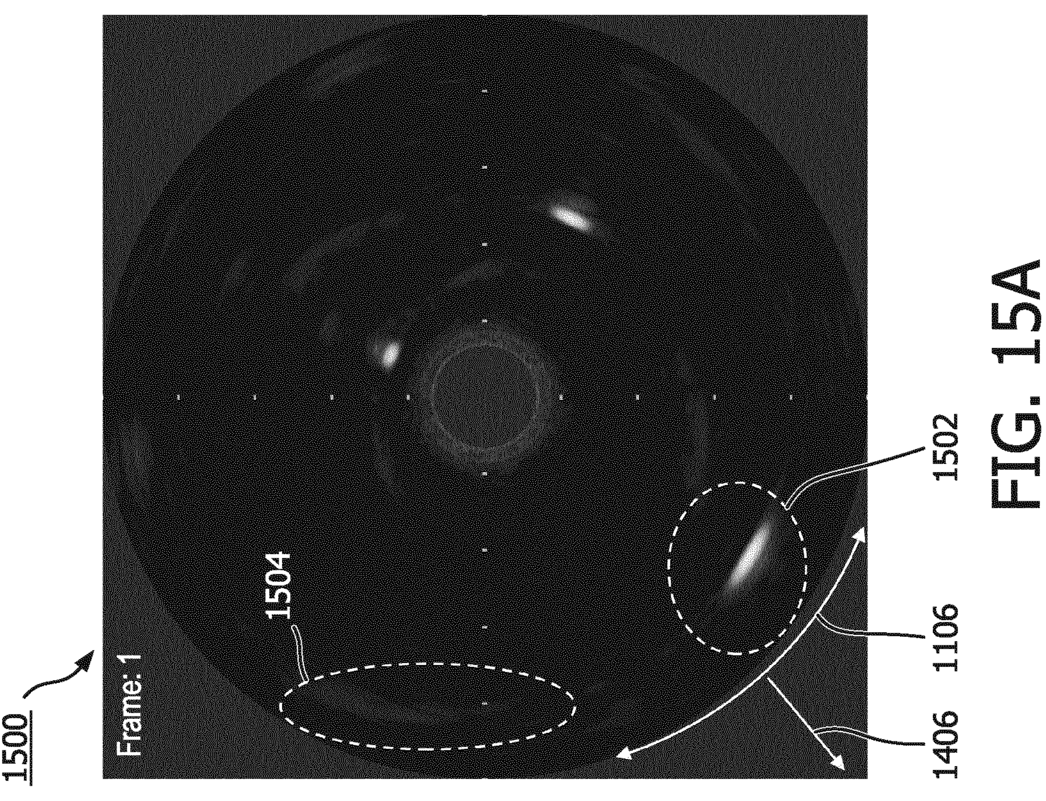

FIGS. 15A-15B illustrate exemplary ultrasound images (e.g., B-mode ultrasound images) of a common target generated in accordance with the techniques described herein. FIGS. 15A-15B facilitate a comparison of first image data A of FIG. 9A with fourth image data D of FIG. 9A. In particular, FIGS. 15A-15B facilitate a comparison of an ultrasound image generated based on the first image data A of FIG. 9A with an ultrasound image generated based on the fourth image data D of FIG. 9A. In this regard, FIG. 15A illustrates an ultrasound image 1500 that is identical to the ultrasound image 800 of FIG. 8, the ultrasound image 1100 of FIG. 11A, and the ultrasound image 1400 of FIG. 14A and may be generated based on processing (e.g., envelope detection, time gain control, scan conversion, and/or the like) of the first image data A of FIGS. 9A-9B. To that end, the ultrasound image 1500 may be generated by the signal pathway 300 of FIG. 3. FIG. 15B illustrates an ultrasound image 1520 generated based on processing (e.g., envelope detection, time gain control, scan conversion, and/or the like) of the fourth image data D of FIGS. 9A-9B. That is, for example, the ultrasound image 1520 may be generated based on performing a second filtering and a second apodization on ultrasound data. For instance, the ultrasound image 1520 may be generated based on applying a whitened bandpass filter (e.g., via the whitened bandpass filter 916) and performing a beamforming with whitened apodization (e.g., at the beamforming with whitened apodization operation 914) on the ultrasound data. Moreover, the ultrasound image 1500 and the ultrasound image 1520 are generated with respect to different apertures. For instance, the ultrasound image 1500 is generated with a 14-element transmit aperture and a 14-element receive aperture, and the ultrasound image 1520 is generated with a 20-element transmit aperture and a 14-element receive aperture. Further, while the fourth image data D is described as optionally being generated based on performing a minimum operation (e.g., via the minimum operation module 920) with respect to first filtered ultrasound data (e.g., filtered data 912) and second filtered ultrasound data (e.g., whitened data 918), the ultrasound image 1520 is generated without performing a minimum operation with respect to the first filtered ultrasound data and the second filtered ultrasound data.

In comparison with the ultrasound image 1500, the ultrasound image 1520 has both a greater axial resolution and a greater lateral resolution. The difference in axial resolution and lateral resolution may be observed with respect to region 1502 of the ultrasound image 1500 and the corresponding region 1522 of the ultrasound image 1520. For instance, the region 1522 of the ultrasound image 1520 has sharper edges along both an axial axis 1406 and a lateral axis 1106 than the corresponding region 1402 of the ultrasound image 1400.

In further comparison with the ultrasound image 1500, the ultrasound image 1520 includes an increased level of side and/or grating lobes (e.g., image artifacts). For instance, in comparison with the region 1504 of the ultrasound image 1500, an intensity of the lobe shown in the corresponding region 1524 of the ultrasound image 1520 is increased. Thus, while the lateral and axial resolution are improved within the ultrasound image 1520, the signal-to-noise ratio of the ultrasound image 1520 is lower within the ultrasound image 1520 than the ultrasound image 1500.

With reference now to FIG. 9B, to improve lateral and axial resolution while mitigating image artifacts (e.g., maintaining a signal-to-noise ratio above a particular level), the image data generated with different combinations of filters and apodizations may be combined. More specifically, a minimum operation may be performed with respect to the image data generated with different combinations of filters and apodizations. Again, while the signal pathway 900 is illustrated and described as including two types of filters and two types of apodization functions such that four sets of image data (e.g., image data A-D) are generated, it may be appreciated that any suitable number sets of image data may generated and combined within the signal pathway 900. Further, while embodiments are described as combining each of the image data generated within the signal pathway, any subsets of the image data may be combined. In the illustrated embodiment, a minimum operation may be performed with respect to the first image data A, second image data B, third image data C, the fourth image data D, or a combination thereof via a minimum operation module 920. As described with respect FIG. 9A, the minimum operation module 920 may combine any of the image data A-D based on the minimum operation, such as a minimum intensity projection. As such, the minimum operation module 920 may suppress and/or minimize an artifact, such as Gibbs ringing and/or a side and/or grating lobe, in an ultrasound image resulting from the image data A-D. In particular, the minimum operation module 920 may preserve a tightened main lobe and suppress side and/or grating lobes both axially and laterally. Moreover, while the module 920 and/or the combination of image data is described herein with respect to a minimum operation, such as a minimum intensity projection, embodiments are not limited thereto. In this regard, any combination of the image data A-D may be combined using linear combination, such as a linear combination based on sorting, or any other suitable techniques.

In some embodiments, before the minimum operation is performed, a respective gain of each of the first through fourth image data A-D may be adjusted (e.g., normalized) such that a mean intensity of each of the first through fourth image data A-D is approximately equal. For instance, the image data A-D may be provided to a range-based gain adjustment module 922, which may be configured to adjust a gain of the image data A-D. In some embodiments, the common level may be determined based on one of the image data A-D. For instance, in some embodiments, the range-based gain adjustment module 922 may adjust the gain of the second image data B, the third image data C, and the fourth image data D to be normalized with respect to the first image data A. Additionally or alternatively, the gain of the image data A-D may be adjusted with respect to predetermined (e.g., preconfigured) normalization levels.

In some embodiments, a processor circuit, such as processor circuit 210 of FIG. 2, may implement the range-based gain adjustment module 922. In some embodiments, for example, a GPU may perform gain adjustment on the image data A-D. Further, while separate range-based gain adjustment modules 922 are illustrated for a respective one of the image data A-D, it may be appreciated that, in some embodiments, the signal pathway 900 may include additional or fewer range-based gain adjustment modules 922. In some embodiments, for example, the signal pathway 900 may include a single range-based gain adjustment module 922 configured to adjust the gain of each of the image data A-D.

The signal pathway 900 may further include a final gain adjustment module 924. The final gain adjustment module 924 may be configured to adjust a gain of the image data produced based on a combination of the image data A-D (e.g., a gain of the output of the minimum operation module 920). In some embodiments, the final gain adjustment module 924 may adjust the gain of this image data for suitable display at the display 330, for example. In some embodiments, a processor circuit, such as processor circuit 210 of FIG. 2, may implement the final gain adjustment module 924. In some embodiments, for example, a GPU may perform the operations of the final gain adjustment module 924. As further illustrated, the final gain adjustment module 924 may output final beamformed data 926.

To generate an ultrasound image 928 (e.g., a B-mode ultrasound image), the signal pathway 900 may perform envelope detection, time gain control, scan conversion, log compression, and/or the like on the final beamformed data 926. To that end, the signal pathway 900 may further include an envelope detection module 322, a time gain control module 324, a scan conversion module 326, and/or the like, as described above with respect to FIG. 3. The signal pathway 900 may further output the generated ultrasound image 928 to a display 330 (e.g., an electronic display).

The signal pathway 900 may include additional components and/or operations, and/or one or more of the components and/or operations may be omitted, performed in a different order, or performed concurrently. Moreover, while particular components and/or operations are illustrated as separate, one or more components and/or operations may be combined. Further, certain components, such as the beamforming with apodization operation 318 are illustrated with duplicates within FIGS. 9A-9B for clarity. It may be appreciated that such repeated components and/or operation may be a single component and/or operation and/or may be separate components and/or operations.

Figures 16A, 16B, 16C:
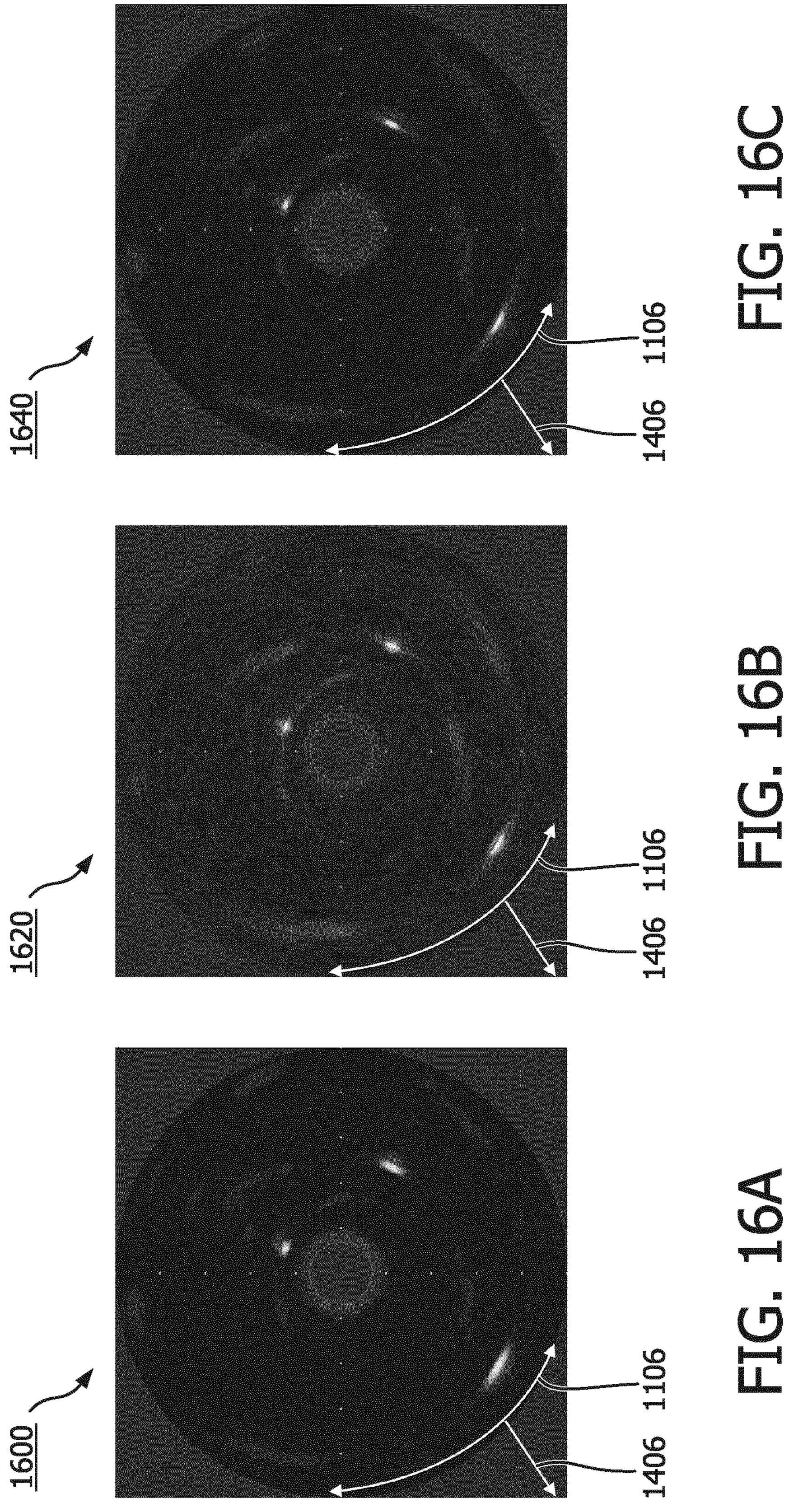
FIGS. 16A-16C illustrate ultrasound images, according to aspects of the present disclosure.

FIGS. 16A-16C illustrate exemplary ultrasound images (e.g., B-mode ultrasound images) of a common target generated in accordance with the techniques described herein. FIGS. 16A-16C facilitate a comparison between an ultrasound image generated based on the first image data A of FIG. 9A, an ultrasound image generated based on the fourth image data D of FIG. 9A, and an ultrasound image generated based on the first, second, third, and fourth image data A-D of FIGS. 9A-B. In this regard, FIG. 16A illustrates an ultrasound image 1600 that is identical to the ultrasound image 800 of FIG. 8, the ultrasound image 1100 of FIG. 11A, the ultrasound image 1400 of FIG. 14A, and the ultrasound image 1500 of FIG. 15A and may be generated based on processing (e.g., envelope detection, time gain control, scan conversion, and/or the like) of the first image data A of FIGS. 9A-9B. To that end, the ultrasound image 1600 may be generated by the signal pathway 300 of FIG. 3. FIG. 16B illustrates an ultrasound image 1620 that is identical to the ultrasound image 1520 of FIG. 15B and may be generated based on processing (e.g., envelope detection, time gain control, scan conversion, and/or the like) of the fourth image data D of FIGS. 9A-9B. FIG. 16C illustrates an ultrasound image 1640 that is generated based on processing (e.g., range-based gain adjustment, performing a minimum operation, envelope detection, time gain control, scan conversion, and/or the like) of the first through fourth image data A-D of FIGS. 9A-9B. That is, for example, the ultrasound image 1640 may correspond to an image generated based on a minimum operation performed with respect to images A-D. To that end, the ultrasound image 1640 may correspond to the image 928 generated and output to a display by the signal pathway 900 of FIGS. 9A-9B.

In comparison with the ultrasound image 1600, the ultrasound image 1640 has both a greater axial resolution and a greater lateral resolution. Further, in comparison with the ultrasound image 1620, the signal-to-noise ratio of the ultrasound image 1640 is greater. That is, for example, the ultrasound image 1640 includes a lower level of image artifacts (e.g., Gibbs ringing and/or side and/or grating lobes) than the ultrasound image 1620. In this regard, the ultrasound image 1640 demonstrates that by performing a minimum operation (e.g., via minimum operation module 920), the lateral resolution and axial resolution improvements shown and described with respect to the ultrasound image 1620 may be persevered while image artifacts may also be mitigated. That is, for example, the minimum operation may preserve a tightened main lobe and suppress side and/or grating lobes both axially and laterally, as shown in FIG. 16C.

Figure 17:
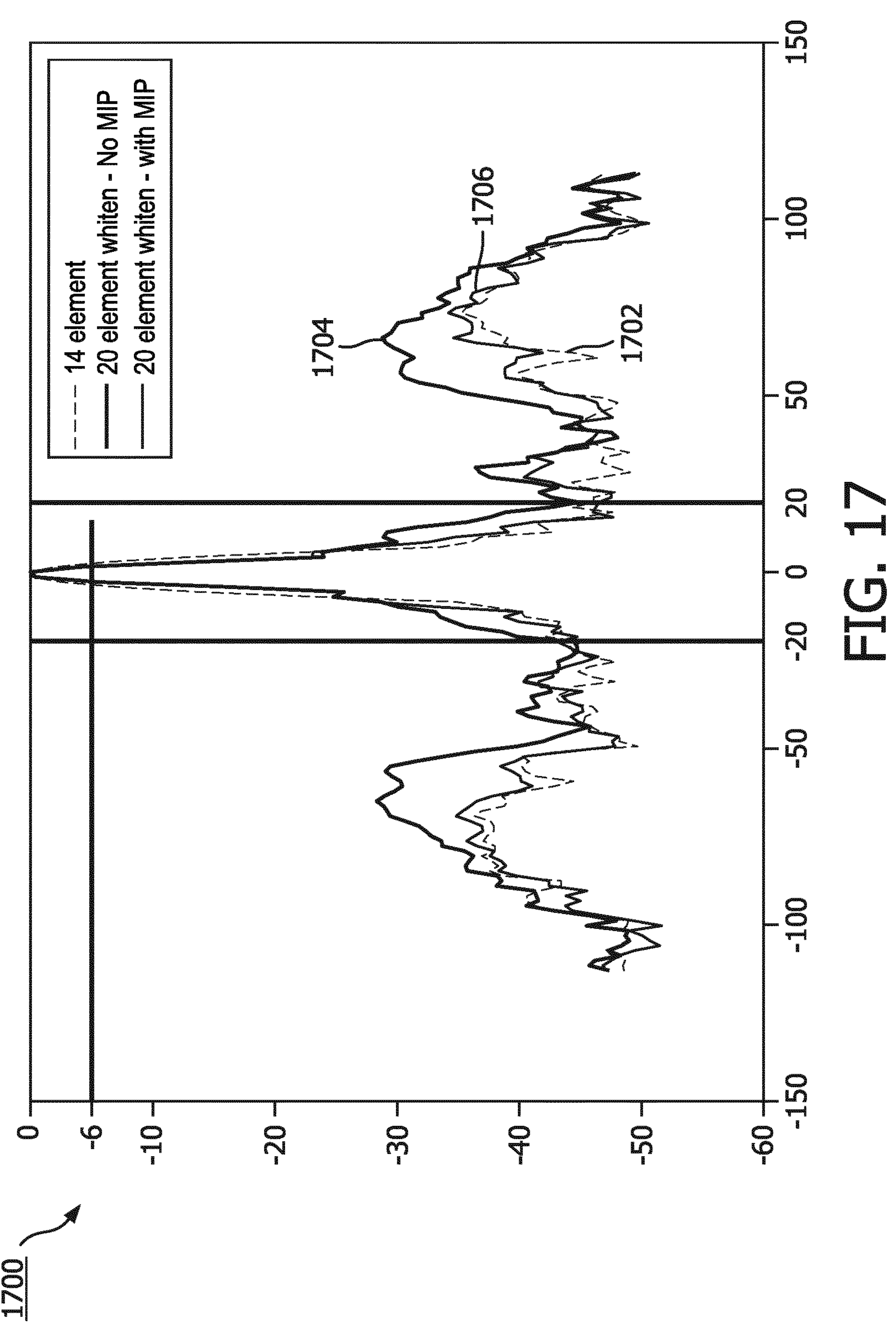
FIG. 17 is a plot of point spread functions, according to aspects of the present disclosure.

A further comparison of ultrasound image generation techniques is illustrated in FIG. 17. FIG. 17 illustrates a plot 1700 of point spread functions (PSFs) of ultrasound images generated according to the techniques described herein. In particular, FIG. 17 illustrates a first curve 1702, which corresponds to the point spread function of an ultrasound image generated according to the techniques described with respect to the signal pathway 300 of FIG. 3, such as image 328, image 800, and/or the like. The plot 1700 further includes a curve 1704, which corresponds to the point spread function of an ultrasound image generated according to the techniques described with respect to the fourth image data D, such as image 1520, image 1620, and/or the like. Further, the plot 1700 includes a curve 1706, which corresponds to the point spread function of an ultrasound image generated according to the techniques described with respect to the signal pathway 900 of FIGS. 9A-9B, such as image 928, image 1640, and/or the like. In particular, the curve 1706 corresponds to an image generated based on a minimum operation applied to a set of different image data (e.g., image data A-D). Moreover, the curve 1702 corresponds to a first aperture (e.g., a 14-element transmit aperture and a 14-element receive aperture), and the curves 1704 and 1706 correspond to a second aperture (e.g., a 20-element transmit aperture and a 14-element receive aperture). The x-axis of the plot 1700 is distance in some arbitrary units, and the y-axis of the plot 1700 is intensity in some arbitrary units, such as decibels (dB).

The plot 1700 demonstrates that the axial and lateral resolution corresponding to both curves 1704 and 1706 is greater than the axial and lateral resolution corresponding to the curve 1702. Further, the plot 1700 illustrates that the mean and max grating lobe energy of the curve 1706 is less than the mean and max grating lobe energy of the curve 1704. In this way, the plot 1700, like the images shown in FIGS. 16A-C, shows that the generation of an ultrasound image involving a combination of different filters, different apodization functions, and a minimum operation improves axial and lateral resolution of the image while mitigating (e.g., suppressing) artifacts (e.g., noise).

Figure 18:
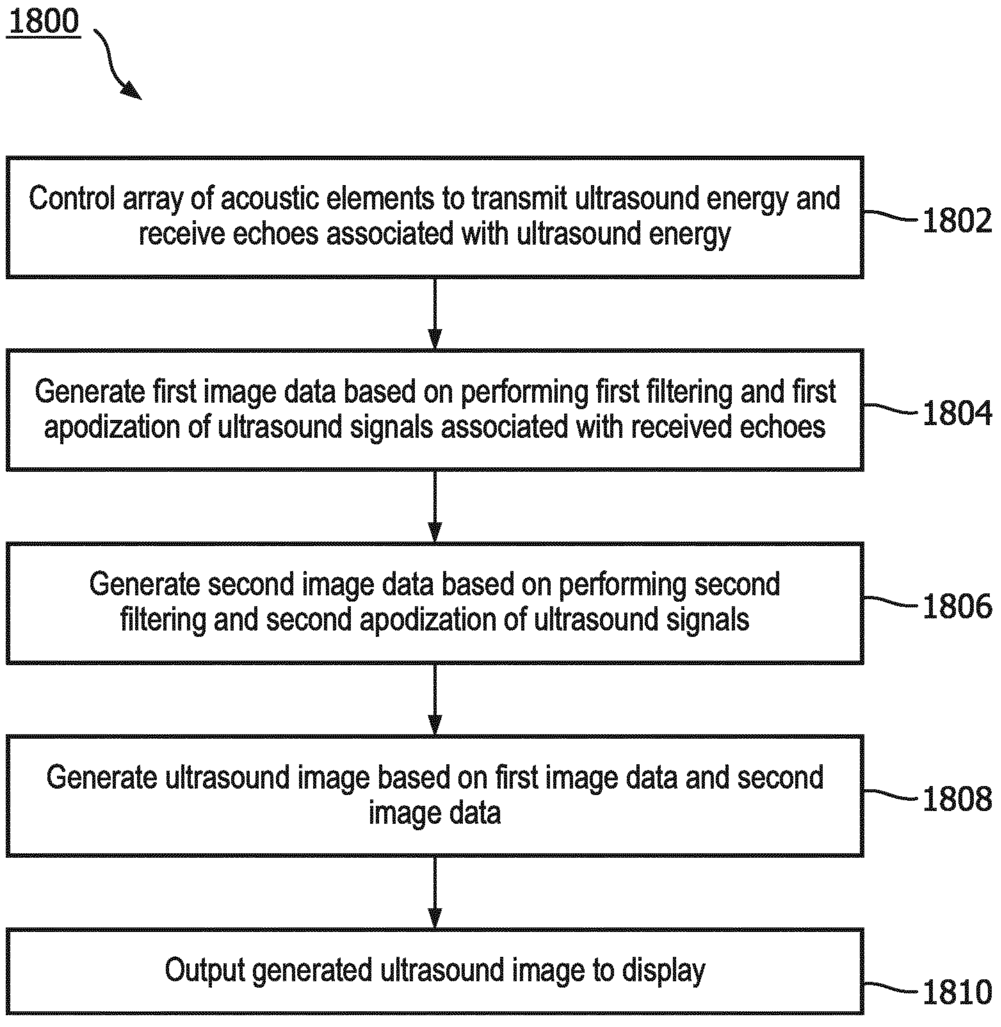
FIG. 18 is a flow diagram of a method for generating an ultrasound image, according to aspects of the present disclosure.

FIG. 18 is a flow diagram of a method 1800 of generating an ultrasound image with a relatively high lateral resolution and a relatively high axial resolution, according to aspects of the present disclosure. As illustrated, the method 1800 includes a number of enumerated steps, but embodiments of the method 1800 may include additional steps before, after, or in between the enumerated steps. In some embodiments, one or more of the enumerated steps may be omitted, performed in a different order, or performed concurrently. The steps of the method 1800 can be carried out by any suitable component within the ultrasound imaging system 100 and all steps need not be carried out by the same component. In some embodiments, one or more steps of the method 1800 can be performed by, or at the direction of, a processor circuit of the ultrasound imaging system 100, including, e.g., the processor 260 (FIG. 2) or any other component.

At step 1802, the method 1800 involves controlling an array of acoustic elements to transmit ultrasound energy and receive echoes associated with ultrasound energy. In some embodiments, for example, the ultrasound imaging system 100 may control the transducer array 124 to transmit ultrasound energy using an array of acoustic elements. In particular, the ultrasound energy may be transmitted via an aperture that includes a quantity of acoustic elements, as described with respect to FIGS. 5 and 6. Further, step 1802 may involve receiving echoes associated with the ultrasound energy. For instance, the array of acoustic elements may be controlled to receive the echoes associated with the ultrasound energy using the aperture of acoustic elements.

In some embodiments, a first quantity of elements of the acoustic array may be used as a transmit aperture to transmit the ultrasound energy and as a receive aperture to receive the associated echoes. As an illustrative example, a 14-element transmit aperture of the array of acoustic elements may be controlled to transmit the ultrasound energy, and a 14-element return aperture of the array of acoustic elements may be controlled to receive the echoes associated with the ultrasound energy. Additionally or alternatively, a first quantity of elements of the acoustic array may be used as a transmit aperture to transmit the ultrasound energy, and a second quantity of elements of the array of acoustic elements may be used as a receive aperture to receive the associated echoes. As an illustrative example, a 20-element transmit aperture of the array of acoustic elements may be controlled to transmit the ultrasound energy, and a 14-element return aperture of the array of acoustic elements may be controlled to receive the echoes associated with the ultrasound energy. Moreover, in some embodiments, separate data acquisitions (e.g., transmission of ultrasound energy and receipt of echoes) may be used to produce ultrasound data (e.g., ultrasound signals) associated with different respective apertures, such as a 20-element or a 14-element aperture. In some embodiments, a common data acquisition (e.g., transmission of ultrasound energy and receipt of echoes) may be used to produce separate apertures, such as a 20-element and a 14-element aperture. For instance, a 20-element transmit aperture may be used to produce ultrasound data corresponding to an aperture involving a 20-element transmit aperture and a 14-element receive aperture, as well as ultrasound data corresponding to an aperture involving a 14-element transmit aperture and a 14-element receive aperture.

At step 1804, the method 1800 involves generating first image data based on performing first filtering and first apodization of the ultrasound signals associated with the received echoes. The first image data may be associated with a first resolution (e.g., a first axial resolution and a first lateral resolution). The first filtering may correspond to a first filter configured to pass a first set of frequencies such that the first set of frequencies is emphasized with respect to a different, second set of frequencies. In particular, the first filtering may correspond to a first filter configured to emphasize a center frequency of the ultrasound signals and de-emphasize an off-center frequency of the ultrasound signals. The filter may be a low-pass filter, a bandpass filter, or a high-pass filter. Moreover, the filter may operate on real-valued or complex-valued data associated with the ultrasound signals, such as the RF data 310 and/or RF data 910 or the IQ data 316, respectively. In some embodiments, the first filter may have a frequency response similar to the plot 400 of FIG. 4.

The first apodization may be associated with a first aperture, such as an aperture using the first quantity of acoustic elements for a transmit and a receive aperture described above (e.g., a 14-element transmit and a 14-element receive aperture). Further, the first apodization may emphasize (e.g., pass and/or amplify) a first set of spatial frequencies of the ultrasound signals, such as spatial frequencies corresponding to acoustic elements within a certain distance to a center of the aperture, and the first apodization may de-emphasize a second set of spatial frequencies of the ultrasound signals, such as spatial frequencies corresponding to acoustic elements beyond (e.g., outside) the distance to the center. In this regard, the first apodization may weight ultrasound signals corresponding to a first subset of the array of acoustic elements (e.g., corresponding to the first set of spatial frequencies) with a first weight. The first apodization may further weight ultrasound signals corresponding to a different, second subset of the array of acoustic elements (e.g., corresponding to the second set of spatial frequencies) with a second weight less than the first weight, where the first subset corresponds to the acoustic elements within the distance to a center of an aperture and the second subset corresponds to the acoustic elements outside the distance. More specifically, performing the first apodization may involve applying a first apodization function, such as the raising cosine function shown in equation 1 and illustrated in FIG. 7B, to the ultrasound signals. To that end, the first apodization may be performed in accordance with the beamforming with apodization operation 318 described above.

In some embodiments, the first image data generated at step 1804 may correspond to the first image data A described with respect to FIGS. 9A-9B. In that regard, the generation of the first image data at step 1804 may additionally or alternatively involve demodulation (e.g., via IQ demodulation module 314) or other suitable image processing operations.

At step 1806, the method 1800 involves generating second image data based on performing second filtering and second apodization of the ultrasound signals associated with the received echoes. In some embodiments, the second image data may be different than the first image data. More specifically, the second image data may be associated with a second resolution (e.g., a second axial resolution and a second lateral resolution), which may be different than the first resolution. To that end, at least one of the second axial resolution or the second lateral resolution of the second image data may be different from the corresponding first axial resolution or the corresponding first lateral resolution of the first image data. For instance, the at least one of the second axial resolution or the second lateral resolution of the second image data may exceed the corresponding first axial resolution or the corresponding first lateral resolution of the first image data. In this regard, at least one of the second filtering or the second apodization may be different than the first filtering or the first apodization, respectively. To that end, while the second filtering or the second apodization may be the same as the first filtering or the first apodization, respectively, the combination of the second filtering and the second apodization may be different than the combination of the first filtering and the first apodization. In this way, the second image data may correspond to the second image data B, the third image data C, or the fourth image data D of the FIGS. 9A-9B. As illustrated by FIG. 9A, the second image data may thus be generated on a different signal pathway, such as a different signal pathway within the signal pathway 900, than the first image data. The generation of the second image data at step 1806 may additionally or alternatively involve demodulation (e.g., via IQ demodulation module 314) or other suitable image processing operations.

In some embodiments, the second filtering may correspond to a second filter configured to de-emphasize the first set of frequencies and emphasize the different, second set of frequencies described above with respect to the first filter. In particular, the second filtering may correspond to a second filter configured to de-emphasize a center frequency of the ultrasound signals and emphasize an off-center frequency of the ultrasound signals. The filter may be a low-pass filter, a bandpass filter, or a high-pass filter. Moreover, the filter may operate on real-valued or complex-valued data associated with the ultrasound signals, such as the RF data 310 and/or RF data 910 or the IQ data 316, respectively. In some embodiments, the second filter may be a whitened and/or whitening filter. For instance, the second filter may have a frequency response similar to the plot 1200 of FIG. 12.

The second apodization may be associated with a second aperture that is different from the first aperture. In some embodiments, the second aperture may use a different quantity of elements than the first aperture. For instance, the second aperture may use the first quantity of acoustic elements for a transmit aperture and a second quantity of acoustic elements for a receive aperture described above (e.g., a 20-element transmit and a 14-element receive aperture). Further, the second apodization may emphasize (e.g., pass and/or amplify) the second set of spatial frequencies of the ultrasound signals, and the second apodization may de-emphasize the first set of spatial frequencies of the ultrasound signals. In this regard, the second apodization may weight ultrasound signals corresponding to the first subset of the array of acoustic elements (e.g., corresponding to the first set of spatial frequencies) with a third weight. The first apodization may further weight ultrasound signals corresponding to the second subset of the array of acoustic elements with a fourth weight greater than the third weight. More specifically, performing the second apodization may involve applying a second apodization function, such as the inversed Hann window shown in equation 2 and illustrated in FIG. 10B, to the ultrasound signals. To that end, the second apodization function may be a whitened and/or whitening apodization function. Moreover, the second apodization may be performed in accordance with the beamforming with whitened apodization operation 914 described above.

At step 1808, the method 1800 involves generating an ultrasound image based on the first image data and the second image data. More specifically, the ultrasound image may be generated based on the first image data and the second image data such that the ultrasound image includes a third resolution (e.g., a third axial resolution and a third lateral resolution) different than at least one of the first resolution or the second resolution. For instance, the third axial resolution may be different than the second axial resolution or the first axial resolution and/or the third lateral resolution may be different than the second lateral resolution or the first lateral resolution. In particular, the third axial resolution may exceed at least one of the second axial resolution or the first axial resolution, and the third lateral resolution may exceed at least one of the second lateral resolution or the first lateral resolution.

In some embodiments, the ultrasound image may be generated based on a minimum operation, such as a minimum intensity projection operation, performed with respect to the first image data and the second image data. Further, in some embodiments, the ultrasound image may be generated based on adjustment of the gain of the first image data and/or the second image data. For instance, before the minimum operation is performed, the mean level intensity of the first image data and/or the mean level intensity of the second image data may be adjusted (e.g., via gain adjustment) to be approximately equal. As described with respect to FIG. 9B, for example, a range-based gain adjustment module 922 may adjust the gain of the first image data and/or the second image data. As further illustrated and described with respect to FIG. 9B, the ultrasound image may be generated based on additional image processing, such as a final gain adjustment (e.g., via final gain adjustment module 924), envelope detection (e.g., via envelope detection module 322), time gain control adjustment (e.g., via time gain control module 324), scan conversion (e.g., via scan conversion module 326), log compression, and/or the like.

Further, in some embodiments, the ultrasound image may additionally or alternatively be generated based on other image data combination techniques. For instance, in some embodiments, the ultrasound image may be generated based on a sum of the first image data and the second image data, an averaging of the first image data with the second image data, and/or the like.

Moreover, while image generation based on first and second image data is described with respect to step 1808, any quantity of image data may be used. In particular, number of filters, apodizations, and/or combinations of filters and apodizations may be employed to generate different sets of image data, and an ultrasound image may be generated based on one or more of these sets. For instance, with respect to FIGS. 9A-9B, an ultrasound image may be generated based on four different sets of image data (e.g., image data A-D), and in other embodiments three, five, six, ten, and/or the like set of image data may be used.

At step 1810, the method 1800 involves outputting the generated ultrasound image to a display. For instance, the generated ultrasound image may be output to a display in communication with a processor circuit (e.g., processor circuit 210). The generated ultrasound image may be output to the monitor 108 of the ultrasound system 100, which may correspond to the display 330 illustrated in FIGS. 3 and 9B. Further, the generated ultrasound image output to the display may have an axial resolution and/or a lateral resolution exceeding a corresponding axial resolution or a corresponding lateral resolution of an ultrasound image generated without the second filtering and/or second apodization of the ultrasound signals, such as an ultrasound image generated based solely on the first image data.

Further, in some embodiments, the method 1800 and/or the step 1806 may be performed in response to a user input at the ultrasound imaging system 100. For instance, generation of the second image data and/or the performance of the method 1800 may be in response to an input to generate an ultrasound image in accordance with the techniques described herein (e.g., with a combination of apodizations and filters). In some embodiments, for example, the ultrasound imaging system 100 may selectively generate an ultrasound image according to different techniques based on the user input. For instance, the ultrasound imaging system 100 may selectively use the signal pathway 300 or the signal pathway 900 to generate an ultrasound image. Additionally or alternatively, the characteristics of combinations of filtering and apodizations may be tuned based on a user input. For example, a user may select between generating an image with increased lateral resolution (e.g., in accordance with the techniques described with respect to second image data B), with increased axial resolution (e.g., in accordance with the techniques described with respect to second image data C), or both (e.g., in accordance with the techniques described with respect to second image data D). The user input may further adjust characteristics of the filters and/or apodizations to dynamically increase resolution and/or minimize image artifacts.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An ultrasound imaging system, comprising:

an array of acoustic elements configured to transmit ultrasound energy and receive echoes associated with the ultrasound energy; and a processor circuit in communication with the array of acoustic elements and configured to:

receive, from the array of acoustic elements, ultrasound signals associated with the received echoes, wherein the ultrasound signals correspond to at least one aperture of the array of acoustic elements;

process the same ultrasound signals in different signal processing pathways to generate an individual ultrasound image; and output the individual ultrasound image to a display in communication with the processor circuit, wherein, to process the same ultrasound signals in the different signal processing pathways, the processor circuit is configured to:

generate, in a first signal processing pathway, first image data based on applying a first filter to the same ultrasound signals and performing a first apodization on the same ultrasound signals, wherein the first filter is configured to emphasize a first set of frequencies of the same ultrasound signals, wherein the first filter is distinct from the first apodization, wherein the first apodization is configured to emphasize a first portion of the same ultrasound signals corresponding to one or more acoustic elements comprising a first physical location within the at least one aperture;

generate, in a different, second signal processing pathway, different, second image data based on applying a second filter to the same ultrasound signals and performing a second apodization on the same ultrasound signals, wherein the second filter is configured to emphasize a different, second set of frequencies of the same ultrasound signals, wherein the second filter is distinct from the second apodization, wherein the second apodization is configured to emphasize a second portion of the same ultrasound signals corresponding to one or more acoustic elements comprising a different, second physical location within the at least one aperture;

generate the individual ultrasound image based on a combination of the first image data and the second image data.

2. The ultrasound imaging system of claim 1, wherein the processor circuit is configured to perform a minimum intensity projection (MIP) operation on the first image data and the second image data, wherein the MIP operation is configured to reduce at least one of a side lobe artifact, a grating lobe artifact, or a Gibbs ringing artifact in the individual ultrasound image.

3. The ultrasound imaging system of claim 1, wherein the at least one aperture comprises a first aperture and a different, second aperture, wherein the processor circuit is further configured to:

perform the first apodization with respect to the first aperture; and perform the second apodization with respect to the second aperture.

4. The ultrasound imaging system of claim 1, wherein the first apodization comprises a first apodization function configured to:

apply a first weight to the same ultrasound signals corresponding to the one or more acoustic elements comprising the first physical location within the at least one aperture; and apply a second weight less than the first weight to the same ultrasound signals corresponding to the one or more acoustic elements comprising the second physical location within the at least one aperture.

5. The ultrasound imaging system of claim 4, wherein the second apodization comprises a second apodization function configured to:

apply a third weight to the same ultrasound signals corresponding to the one or more acoustic elements comprising the first physical location within the at least one aperture; and apply a fourth weight greater than the third weight to the same ultrasound signals corresponding to the one or more acoustic elements comprising the second physical location within the at least one aperture.

6. The ultrasound imaging system of claim 1, wherein the processor circuit is further configured to generate third image data based on applying a third filter to the same ultrasound signals and performing a third apodization on the same ultrasound signals, wherein the third image data is different than the first image data and the second image data, and wherein the processor circuit is configured to generate the individual ultrasound image further based on the third image data.

7. The ultrasound imaging system of claim 1, wherein the processor circuit is configured to provide a depth-dependent filtering, wherein, to provide the depth-dependent filtering, the processor circuit is configured to:

divide the same ultrasound signals based on a first depth, a second depth, and a third depth, wherein the first depth is closer to the array of acoustic elements than the second depth and the third depth; and at least one of:

apply the first filter to ultrasound signals of the first depth and apply the second filter to ultrasound signals of the second depth; or apply a first version of the second filter to the ultrasound signals of the second depth and a second version of the second filter to ultrasound signals of the third depth.

8. The ultrasound imaging system of claim 1, wherein the processor circuit is further configured to:

adjust at least one of a gain of the first image data or a gain of the second image data such that a mean level intensity of the first image data and a mean level intensity of the second image data are equal.

9. The ultrasound imaging system of claim 1, wherein the processor circuit is configured to generate the individual ultrasound image further based on performing envelope detection.

10. The ultrasound imaging system of claim 1, wherein the processor circuit is configured to generate the individual ultrasound image further based on performing scan conversion.

11. The ultrasound imaging system of claim 1, wherein the processor circuit comprises a graphics processing unit (GPU).

12. A method, comprising:

controlling an array of acoustic elements in communication with a processor circuit to transmit ultrasound energy and receive echoes associated with the ultrasound energy;

receiving, from the array of acoustic elements, ultrasound signals associated with the received echoes, wherein the ultrasound signals correspond to at least one aperture of the array of acoustic elements;

processing the same ultrasound signals in different signal processing pathways to generate an individual ultrasound image; and outputting the individual ultrasound image to a display in communication with the processor circuit, wherein processing the same ultrasound signals in the different signal processing pathways comprises:

generating, in a first signal processing pathway, first image data based on applying a first filter to the same ultrasound signals and performing a first apodization on the same ultrasound signals, wherein the first filter emphasizes a first set of frequencies of the same ultrasound signals, wherein the first filter is distinct from the first apodization, wherein the first apodization emphasizes a first portion of the same ultrasound signals corresponding to one or more acoustic elements comprising a first physical location within the at least one aperture;

generating, in a different, second signal processing pathway, different, second image data based on applying a second filter to the same ultrasound signals and performing a second apodization on the same ultrasound signals, wherein the second filter emphasizes a different, second set of frequencies of the same ultrasound signals, wherein the second filter is distinct from the second apodization, wherein the second apodization emphasizes a second portion of the same ultrasound signals corresponding to one or more acoustic elements comprising a different, second physical location within the at least one aperture;

generating the ultrasound image based on a combination of the first image data and the second image data.

13. The ultrasound imaging system of claim 1, wherein the second apodization comprises a whitened apodization.

14. The ultrasound imaging system of claim 1, wherein the second apodization is configured to provide a second lateral resolution to the second image data, wherein the second lateral resolution exceeds a first lateral resolution of the first imaging data.

15. The ultrasound imaging system of claim 1, wherein the second filter comprises a whitened filter.

16. The ultrasound imaging system of claim 1, wherein the second filter is configured to provide a second axial resolution to the second image data, wherein the second axial resolution exceeds a first axial resolution of the first imaging data.

17. The ultrasound imaging system of claim 1, further comprising an intravascular ultrasound (IVUS) catheter configured to be positioned inside a blood vessel of a patient, wherein the IVUS catheter comprises the array of acoustic elements in a circumferential arrangement.

18. The ultrasound imaging system of claim 1, wherein an axial resolution of the individual ultrasound image exceeds an axial resolution of the first image data and an axial resolution of the second image data, and wherein a lateral resolution of the individual ultrasound image exceeds a lateral resolution of the first image data and a lateral resolution of the second image data.

19. The ultrasound imaging system of claim 1, wherein the first physical location is within a distance to a center of the at least one aperture such that the one or more acoustic elements corresponding to the first physical location comprise one or more center acoustic elements, wherein the second physical location is outside the distance such that the one or more acoustic elements corresponding to the second physical location comprise one or more off-center acoustic elements.

* * * * *